(12) United States Patent
Rodemund et al.

(10) Patent No.: US 11,534,206 B2
(45) Date of Patent: Dec. 27, 2022

(54) MEDICAL POSITIONING DEVICE

(71) Applicant: PMU Innovations GMBH, Salzburg (AT)

(72) Inventors: Christian Rodemund, Leonding (AT); Johann Fierlbeck, Salzburg (AT)

(73) Assignee: PMU INNOVATIONS GMBH, Salzburg (AT)

(*) Notice: Subject to any disclaimer, the term of this patent is extended or adjusted under 35 U.S.C. 154(b) by 2 days.

(21) Appl. No.: 17/279,832

(22) PCT Filed: Sep. 25, 2019

(86) PCT No.: PCT/EP2019/075827
§ 371 (c)(1),
(2) Date: Mar. 25, 2021

(87) PCT Pub. No.: WO2020/064814
PCT Pub. Date: Apr. 2, 2020

(65) Prior Publication Data
US 2021/0393294 A1    Dec. 23, 2021

(30) Foreign Application Priority Data

Sep. 28, 2018  (EP) ..................................... 18197557
May 8, 2019    (EP) ..................................... 19173256

(51) Int. Cl.
*A61B 17/64*    (2006.01)
*A61B 17/66*    (2006.01)

(52) U.S. Cl.
CPC ...... *A61B 17/6425* (2013.01); *A61B 17/6475* (2013.01); *A61B 17/66* (2013.01)

(58) Field of Classification Search
CPC . A61B 17/6425; A61B 17/6475; A61B 17/66; A61B 17/6466; A61B 17/645; A61B 17/6441

(Continued)

(56) References Cited

U.S. PATENT DOCUMENTS 2,346,346 A *  4/1944  Anderson .......... A61B 17/6441
                                              606/56
6,328,737 B1  12/2001  Moorcroft et al.
2014/0066931 A1*  3/2014  Myers ................ A61B 17/6458
                                              606/59

FOREIGN PATENT DOCUMENTS

GB      538599 A      8/1941
WO   2020064814 A1   4/2020

OTHER PUBLICATIONS

Extended European Search Report for Application No. 18197557.4, dated Mar. 22, 2019, 7 pages.

(Continued)

*Primary Examiner* — Eduardo C Robert
*Assistant Examiner* — Tara Rose E Carter
(74) *Attorney, Agent, or Firm* — Seager, Tufte & Wickhem, LLP

(57) ABSTRACT

The present invention relates to a medical positioning device. In one example, the device comprises comprising a first carriage assembly configured for mounting a first pin, wherein the orientation of the first pin is adjustable by a first spherical joint with three rotational degrees of freedom with an angular range of at least ±10° each, a second carriage assembly configured for mounting a second pin, wherein the orientation of the second pin is adjustable by a second spherical joint with three rotational degrees of freedom with an angular range of at least ±10° each and an extension assembly for adjusting a distance between the first pin and the second pin.

6 Claims, 16 Drawing Sheets

(58) Field of Classification Search
USPC .................................................. 606/54–59
See application file for complete search history.

(56) References Cited

OTHER PUBLICATIONS

International Search Report and Written Opinion for International application No. PCT/EP2019/075827, dated Jan. 7, 2020, 11 pages.

\* cited by examiner

MEDICAL POSITIONING DEVICE

PRIORITY

This application is a US national stage filing of international PCT application PCT/EP2019/075827, filed Sep. 25, 2019, which claims the benefit of priority to European Patent Application Serial No. 18197557.4, filed Sep. 28, 2018, and European Patent Application Serial No. 19173256.9, filed May 8, 2019, which are each incorporated by reference herein in their entirety and for all purposes.

The present invention relates to a medical positioning device that can be used in surgical procedures, particularly orthopedic procedures.

Several medical treatments require the positioning and/or repositioning of body parts of a patient. For example, if a patient suffers from a bone fracture, it may be necessary to reposition the fractured pieces of the bone in order to support and/or assure a healing process with the fractured pieces of the bone in the correct position.

A variety of fracture reduction devices are known in the art. For example, U.S. Pat. No. 6,328,737 B1 discloses a fracture reduction device comprising linear adjustment means for linearly reducing a fractured bone, and an angular adjustment mechanism for angularly reducing a fractured bone. However, the devices known in the art have different drawbacks. The devices are often large and heavy, and the handling is complicated and uncomfortable for a user, e.g. a physician.

It is therefore an object of the present invention to provide a medical positioning device with improved functionality. This is achieved with the inventive medical positioning device according to the claims.

In the following description, the invention will be described with reference to a treatment of a fractured foot. However, the invention is applicable to other repositioning treatments, e.g., of other bones, without departing from the scope of the invention.

A medical positioning device according to the invention may comprise a first carriage assembly configured for mounting a first pin, wherein the spatial orientation of the first pin is adjustable by means of a first spherical joint with at least three rotational and/or pivotable degrees of freedom with an angular range of at least ±10° each. The device may further comprise a second carriage assembly configured for mounting a second pin, wherein the spatial orientation of the second pin is adjustable in by means of a second spherical joint with at least three rotational and/or pivotable degrees of freedom with an angular range of at least ±10° each. Furthermore, the device may have an extension assembly configured for adjusting a distance and/or spatial orientation between the first pin and the second pin.

Particularly, the medical positioning device may be configured for repositioning bones in a patient's body part, preferably for repositioning bones in a human's foot. In the context of the present invention the term "bones" is not only used for complete bones but also for portions or pieces thereof.

The pins serve for attaching the medical positioning device to a patient's body part, e.g., one or more bones, that needs to be repositioned. The pins may be suitable for and configured for being inserted into the patient's body and may be particularly suitable for being inserted into and through a patient's bone. Methods for inserting a pin into a patient's body are known in the art and will therefore not be described in detail. Particularly, the first pin is configured for being inserted on a first side of the body part and the second pin is configured for being positioned at a second side of the body part opposite the first side, such that the body part to be treated is located between the two pins. With this configuration, the medical positioning device may be used to apply forces and moments to the body part between the pins, which enables a user to rearrange the body part, e.g., fractured bone pieces, between the pins by actuating an extension mechanism of the medical positioning device.

In order to perform the rearrangement of the body part between the pins, the first and second pins need to be moved relative to each other. The medical positioning device comprises first and second carriage assemblies for mounting the first and second pins, respectively. The first and second carriage assemblies comprise first and second spherical joints, respectively. The spherical joints may be configured for enabling spatial reorientation of the pins. The spherical joints, and thus the pins, may each have three degrees of freedom, as commonly known for spherical joints. Typically, the range of movement of a spherical joint is limited by the specific geometry of the spherical joint, for example, the configuration of the ball's attachment structure for connection to another member and of the socket of the spherical joint. In the context of the present invention, a spherical joint preferably has a rotational range of 360°, i.e., no limitations, for rotation about its longitudinal axis created by the ball and socket of the joint. The other two rotational or pivotable degrees of freedom, which are preferably rotations or pivotal about two axes that are perpendicular to each other and perpendicular to the longitudinal axis of the spherical joint, preferably have an angular range of at least ±10° each, preferably an angular range of at least ±20° each, more preferably an angular range of at least ±30° each. This enables an angular adjustment of the pins and thus the bones. The maximum angular range for the other two rotational or pivotable degrees of freedom may be ±70° each, or ±60° each, or ±50° each. Also, ranges from ±10°, ±20°, or ±30° up to ±70°, or up to ±60°, or up to ±50° (all permutations) are envisaged.

The medical positioning device may further comprise an extension assembly. By actuating the extension assembly, a user may adjust the distance between the first carriage assembly and the second carriage assembly, thereby adjusting the distance between the first pin and the second pin. This may be achieved by a linear movement of the first carriage assembly relative to the second carriage assembly.

Hence, the medical positioning device may enable an adjustment of the orientation of each of the pins as well as their distance to each other, which allows for a precise repositioning of the attached body parts The extension assembly may be configured for adjusting the distance of the carriage assemblies of the first and second pins relative to each other in a range of at least 2 cm, or at least 4 cm and/or up to 10 cm, or up to 8 cm, or up to 5 cm. Again, all combinations (permutations) of the various lower and upper limits are envisaged.

The medical positioning device, and particularly the spherical joint(s), may be configured for resisting a moment of at least 3 Nm, preferably at least 9.5 Nm, more preferably at least 11 Nm, most preferably at least 12.5 Nm, as applied by the pins. This ensures that the pieces of a fractured bone may be repositioned into the correct locations, even against the forces exerted on the pieces, e.g., by surrounding tissue and during the distraction process.

At least one of the first and second carriage assemblies may comprise a support member configured for mounting the respective pin, for example, at two mounting sites. The mounting sites are preferably separated by 7 to 20 cm, more preferably by 10 to 14 cm. Preferably, both carriage assemblies comprise a respective support member.

The pins may be configured for traversing a patient's body part. The mounting sites of the support member(s) may be configured to be located on different sides of the traversed body part. For example, one of the pins may be configured for traversing the patient's foot from a lateral to a medial side such that one mounting site is located laterally of the foot and the other mounting site is located medially of the foot.

The medical positioning device may comprise a base frame. The first carriage assembly and the second carriage assembly may each be adjustably mounted to the base frame, preferably via first and second carriages, respectively. The base frame may comprise two rods that serve as rails for the first and second carriages. The carriage assemblies, preferably the carriages, may each comprise a fixing assembly for removably fixing the carriage assembly to the base frame. The fixing assembly may comprise a screw, a quick release skewer or the like. The removable fixing assembly ensures that the distance between the carriage assemblies may be adjusted, e.g., for adjusting the medical positioning device to the size of the body region to be treated. Alternatively, one of the carriage assemblies may be non-adjustably mounted to the base frame, preferably via the respective carriage.

Preferably, each support member is mounted to the respective carriage via the respective spherical joint. The at least one support member, preferably both support members, may have any suitable form. Preferably, the form is generally C-shaped, U-shaped, V-shaped or T-shaped. The at least one support member preferably comprises one or more brackets configured for mounting the respective pin at the respective mounting site. Preferably, the at least one support member, preferably each support member, comprises two brackets, one for each mounting site for the associated pin. The bracket's position on the support member may be adjustable. This may provide further flexibility to the device.

Preferably, the support member comprises a spring-screw-mechanism, wherein the spring attaches the bracket to the rest of the support member but allows for a movement of the bracket relative to the rest of the support member that enables the user to insert the pin into an engagement region for the pin. The screw is preferably configured for closing the bracket, thus causing the bracket to fix the support member at the pin The fixation of the pin may be configured for reducing bending of the pin. The support member and the bracket may together form a three point fixation of the pin at each mounting site. This leads to a decrease in bending of the pin in comparison to a single point fixation, for example a hole, at each mounting site. This may be advantageous because the pretension adds stability to the pin. Thus, the pin is less prone to an unwanted deformation due to the forces and moments acting on the pin during the repositioning procedure. It is preferable to have the pin as straight as possible because this helps the physician to identify the position and orientation of the pin inside the patient's body and thus the orientation and position of the body parts to be repositioned. Also a straight pin reduces the deformation of bone volume where the pin penetrates the respective bone. This increases a stable fit of the pin in the bone.

The base frame of the medical positioning device may generate an area and/or volume that is at least partially surrounded by the base frame. For example, if the base frame comprises the two rods as mentioned above, the two rods define an area between them. Similarly, if the base frame comprises three rods, the three rods define a volume between them that has the shape of a prism with a triangular base. The area and/or the volume generated by the base frame is/are preferably free of the pins. This has several advantages. For example, it increases the number of possible orientations that the medical positioning device may have relative to the body portion to be treated. This makes it easier for the user to appropriately attach the device to the patient's body. Furthermore, it increases the adjustability to different body parts such that the device may be not only used for one specific type of repositioning treatment, e.g., repositioning of the fractured bone pieces of a foot, but for several different repositioning treatments of different body types, e.g., also for bones of a leg and/or bones of an arm and/or bones of a hand.

The extension assembly is preferably associated with the first carriage assembly and forms a first extension assembly. Preferably, it comprises a threaded rod coupled to the support member of the first carriage assembly, wherein the medical positioning device is preferably configured for adjusting the distance between the first and second pins by rotational movement between the threaded rod and a counter threading. For example, the first carriage assembly, preferably the carriage of the first carriage assembly, may comprise a screw fence, and the threaded rod is attached to the spherical joint.

The medical positioning device may comprise a second extension assembly associated with the second carriage assembly and may be configured for adjusting the distance between the first and second pins in combination with the first extension assembly. The second extension assembly may be structured equivalent to the first extension assembly.

Particularly, the second extension assembly may comprise a second threaded rod coupled to the support member of the second carriage assembly and a second extension screw mounted on the second threaded rod as well as a second screw fence. The medical positioning device may be configured for adjusting the distance between the first carriage assembly and the second carriage assembly by a movement of the second threaded rod and/or the first threaded rod relative to the respective screw fences by a rotation of the respective screws against the respective screw fences. Preferably, the second carriage assembly, preferably the carriage of the second carriage assembly, comprises the second screw fence.

Alternatively, only one of the carriage assemblies may comprise an extension assembly.

Additionally or alternatively, the second carriage assembly may comprise a force sensor or dynamometer. The force sensor or dynamometer may serve to measure and display a force exerted between the first and second carriage assemblies during a repositioning procedure. The force sensor or dynamometer may comprise a spring and use the principle of a spring balance. However, other force sensors such as a force sensing resistor, an eddy current type absorber, a powdered dynamometer, hysteresis dynamometer, an electric motor/generator dynamometer, and the like are contemplated.

Preferably, each of the spherical joints is arranged to couple the respective support member to the respective carriage, thus providing the flexibility to the system. Preferably, at least one spherical joint, more preferably each of the spherical joints, comprises a ball, a corresponding socket and a locking mechanism configured for reversibly receiving and locking the ball in the socket. This provides additional flexibility to the system. For example, the ball may be attached to the support member, whereas the socket may be coupled to the carriage. With this embodiment, the user may first attach the pins to the body of the patient and then attach the first and second support members to the first and second pins, respectively. Subsequently, the user may attach the first and second support members to the first and second carriages, respectively. This may be preferably achieved by inserting the ball of the spherical joint (located on the support member) into the corresponding socket of the spherical joint (located on the carriage) and locking the ball in the socket by means of the locking mechanism. Ball and socket may also be arranged vice versa, i.e., the ball may be attached to the carriage and the socket may be attached to the support member.

If the socket is configured for being attached to the support member, the threaded rod may be coupled to the ball, i.e., the shaft of the ball, and if the ball of the spherical joint is configured for being attached to the support member, the threaded rod may be coupled to the socket.

The locking mechanism may be implemented in any suitable manner. Preferably, the socket comprises a side opening for inserting the ball such that insertion and removal of the ball into and from the socket is only possible through the side opening of the socket but not in the longitudinal direction. The spherical joint preferably further comprises a locking ring that may be displaced between a closing position and opening position. The spherical joint may comprise a sleeve along a surface of the socket, preferably along the outer surface of the socket and even more preferably along the inner surface of the socket. The sleeve may be configured for at least partially closing the side opening of the socket, when the locking ring is in a closing position, such that the ball may not exit through the side opening. If the sleeve/locking ring is, however, in the opening position, the side opening is not blocked by the sleeve and the ball is free to leave the socket. The locking ring may be biased to the closing position, e.g., by means of a spring. The locking ring may preferably be fixed to the socket with the locking ring—socket—assembly being configured to move relative to the sleeve. Alternatively, the locking ring may be fixed to the sleeve with the locking ring—sleeve—assembly being configured to move relative to the socket.

In an exemplary method of applying the device in a repositioning treatment, a user may first attach the first and second pins at appropriate positions in the patient's body. Then, the user may attach first and second support members to first and second pins, respectively. The user may couple the first and second support members to the first and second carriages, respectively. The coupling of the support members to the respective carriage may occur by coupling of the respective ball and the corresponding socket of the respective spherical joint. As already mentioned, the ball part of the spherical joint may be attached to the support member and the socket part of the spherical joint may be attached to the carriage, or vice versa. First and second carriages may then be coupled to the base frame.

In a preferred embodiment, the base frame or the carriages may be, directly or indirectly, coupled to a fix member that is fixedly installed, such as an operation table, a wall, a floor, a ceiling and the like. In the case of an indirect coupling to the fix member, any suitable intermediate fixation device may be used.

Further features and embodiments are contemplated. For example, the spherical joint may have a different configuration. The alternative spherical joint may also comprise a ball, a corresponding socket and a locking mechanism configured for reversibly locking the ball in the socket. In this embodiment, the socket may be formed by two socket clamps, which are part of and/or attached to the support member. The two socket clamps are connected via a hinge, which allows a shifting of the socket clamps between an open configuration and a closed configuration. In the open configuration, the ball may be inserted or removed, whereas in the closed configuration this is not possible. The spherical joint may comprise a joint screw for fixing the closed configuration in such a way that the ball is fixedly clamped by the socket clamps in a locked configuration. If the joint screw is only slightly loosened, the ball may be moved/rotated while still being clasped by the socket clamps.

The distance between the mounting sites of the respective pin may be adjustable. For example, the support member may comprise first and second support arms configured for mounting the respective pin at first and second mounting sites, respectively. The distance between the mounting sites of the respective pin may be adjustable via adjusting the distance between the first and second support arms. This may be achieved in any possible way. Preferably, the support arms are movably mounted on at least one, preferably two support rods of the support member. Each support arm may comprise a support screw for reversibly fixing the support arm at a desired location along the one or more support rods.

The carriage assembly may be configured for rotating the respective pin about at least a first axis crossing the respective pin. Preferably, the carriage assembly is configured for rotating the respective pin about a first axis and a second axis crossing the pin, preferably in the same point of the pin. Preferably, the rotation about the first axis is independent from the rotation about the second axis. Preferably, these rotations are independent from an actuation of the spherical joint, i.e. these rotations are provided in addition to the flexibility provided by the spherical joint. Preferably, one axis or both axes traverse the body part to be treated, when the medical positioning device is correctly installed. Most preferably, the two axes cross each other in the body part to be treated, thus creating a single pivot point within the body part to be treated. The one axis or two axes may be selected from a longitudinal axis of the medical positioning device that is defined by the axis of the spherical joints and a transversal axis of the medical positioning device that is perpendicular to the longitudinal axis.

The carriage assembly may comprise a sliding carriage configured for engaging with the support member, preferably with a guidance provided at or in the support member. A movement of the support frame along the sliding carriage may provide for rotation about at least one of the longitudinal axis and the transversal axis, preferably about the transversal axis only.

For example, the extension assembly may comprise a sliding carriage, which may in turn be configured for sliding along the support member, preferably along the guidance of the support member. A movement of the support member along the sliding carriage provides for rotation of the support member, and thus the pin, about one of the axes, preferably about the transversal axis. The guidance may be a curvilinear slot in the support member. In order to provide for the curvilinear slot, the support member may have a portion with a respective curvilinear shape. The carriage assembly preferably comprises a transversal fixation element configured for fixing the position of the support member relative to the extension assembly. If the transversal fixation element is in a closed position, the relative position is fixed. If the transversal fixation element is in an open position, the support member, and thus the respective pin, may be moved relative to the extension assembly, which results in the rotation of the pin about the transversal axis.

The carriage assembly may comprise a rotation rod. Rotation of the rotation rod about its longitudinal axis may provide for the rotation of the respective pin about the longitudinal axis of the medical positioning device. The rotation of the rotation rod may be transferred to the pin via the support member. Preferably, the carriage assembly comprises a longitudinal fixation element. If the longitudinal fixation element is in a closed position, a rotation about the longitudinal axis is inhibited. If the longitudinal fixation element is in an open position, a rotation about the longitudinal axis is allowed.

The longitudinal fixation element may also serve as the transversal fixation element. However, it is preferred that the rotation about the longitudinal axis is independent from the rotation about the transversal axis. Hence, it is also preferred that the longitudinal fixation element is independent from the transversal fixation element.

Preferably, as described above, rotations about the two axes are provided by means of one rotation assembly. However, it is also possible to provide separate rotation assemblies, one rotation assembly for each rotation axis, for example one rotation assembly for a rotation about the longitudinal axis and one for the rotation about the transversal axis. The separate rotation assemblies may have similar or different working principles. For example, each rotation assembly may comprise a rotation rod and be configured for providing for a rotation of the pin about the respective axis by means of a rotation of the rotation rod about the respective axis, e.g., as described above.

Further details of the invention will be described with reference to the figures, in which.

Figure 1A:
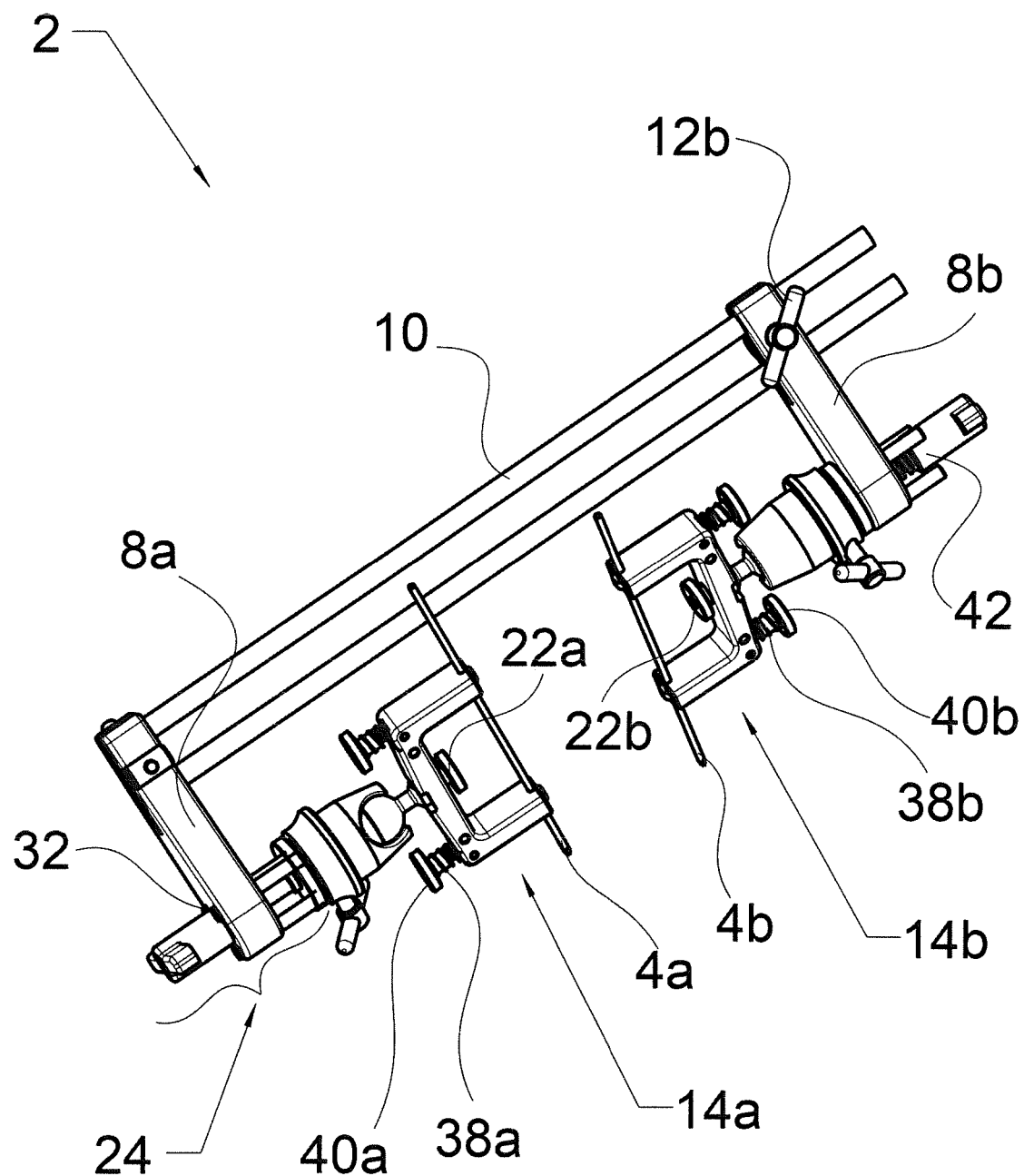
FIG. 1A shows a perspective view of an embodiment of the medical positioning device.

FIGS. 1A-2E show different views of a preferred embodiment of a medical positioning device 2 according to the present invention. FIGS. 1A and 1B show the same perspective view of the device 2, once with the device installed at a human's foot (only the bones of the shank and the foot are shown) and once the device without the human's foot. With respect to the foot in FIG. 1B, the view is an angled bottom up view. FIGS. 2A-2E show the embodiment of FIGS. 1A-1B in several views along different axes through the device for further clarification. The medical positioning device 2 is shown with first and second pins 4a, 4b coupled to first and second carriage assemblies 6a, 6b, respectively. Each carriage assembly 6a, 6b may comprise a carriage 8a, 8b configured for coupling to a base frame 10 (see FIG. 2C). The base frame 10 of the shown embodiment comprises two rods, however, other constructions, e.g., a base frame comprising one rod, three rods, four or more rods and the like, are also contemplated.

Each carriage 8a, 8b may comprise an appropriate number of seats for receiving the respective counterpart of the base frame 10. The illustrated embodiment has two rods of base frame 10 such that movement of the carriage 8a, 8b relative to the base frame 10 is enabled. The carriages 8a, 8b may slide along base frame 10 as indicated by the double arrows in FIG. 2C. This allows for a coarse adjustment of the distance D1 between the first and second carriages 8a, 8b and thus the whole carriage assemblies 6a, 6b. Thus, a user may attach the medical positioning device 2 via the pins 4a, 4b to different body parts, e.g. a foot, a hand, an arm or a leg, and/or two different patients, e.g. an adult or a child, a tall person or a small person.

Once the carriages 8a, 8b are appropriately positioned on the base frame 10 and with respect to one another, the carriages 8a, 8b may be locked by means of a fixing assembly 12a, 12b, such that they cannot move relative to the base frame 10 anymore. As a fixing assembly, any appropriate mechanism may be used. However, a fixing assembly 12a, 12b including a screw for tightening the carriages 8a, 8b around the rods of the base frame 10 is preferred. For example, a quick release skewer may be used.

At least one of the carriage assemblies 6a, 6b may comprise a support member 14a, 14b. Preferably, as shown in the Figures, both carriage assemblies 6 comprise a respective support member 14a, 14b. The support members 14a, 14b may be configured for coupling a respective pin 4a, 4b, preferably at two mounting sites.

Figure 2A:
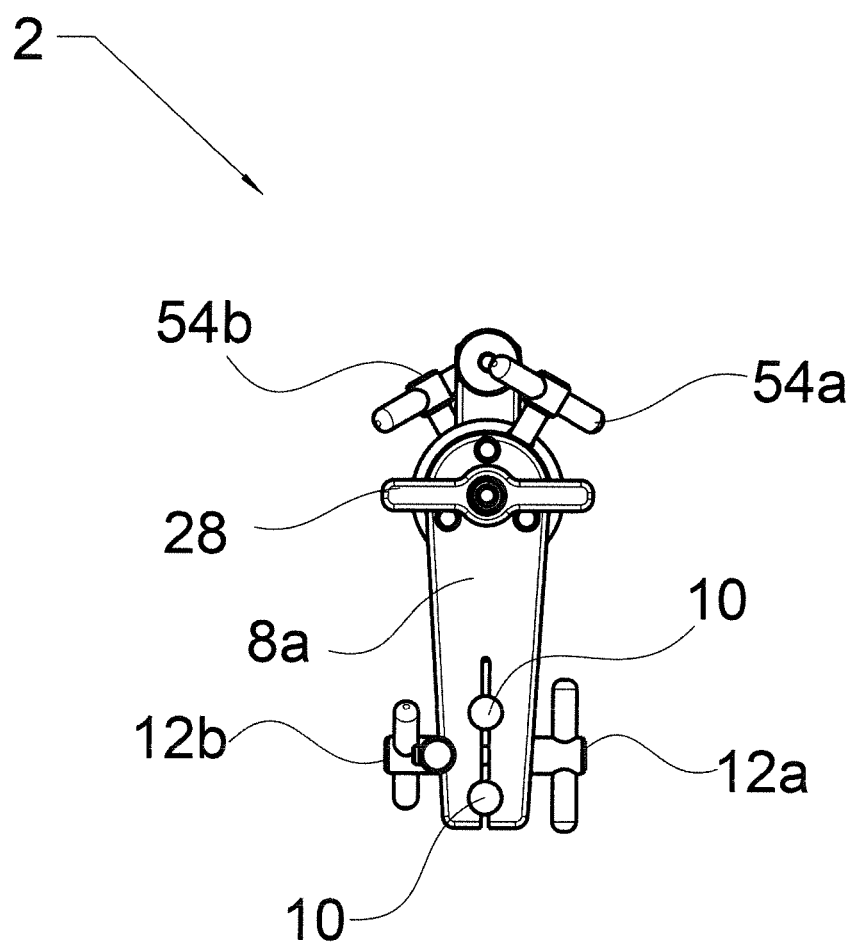
FIG. 2A shows the embodiment of FIGS. 1A and 1B in a view at the first carriage along a longitudinal direction from the first to the second carriage of the device.
Figure 2B:
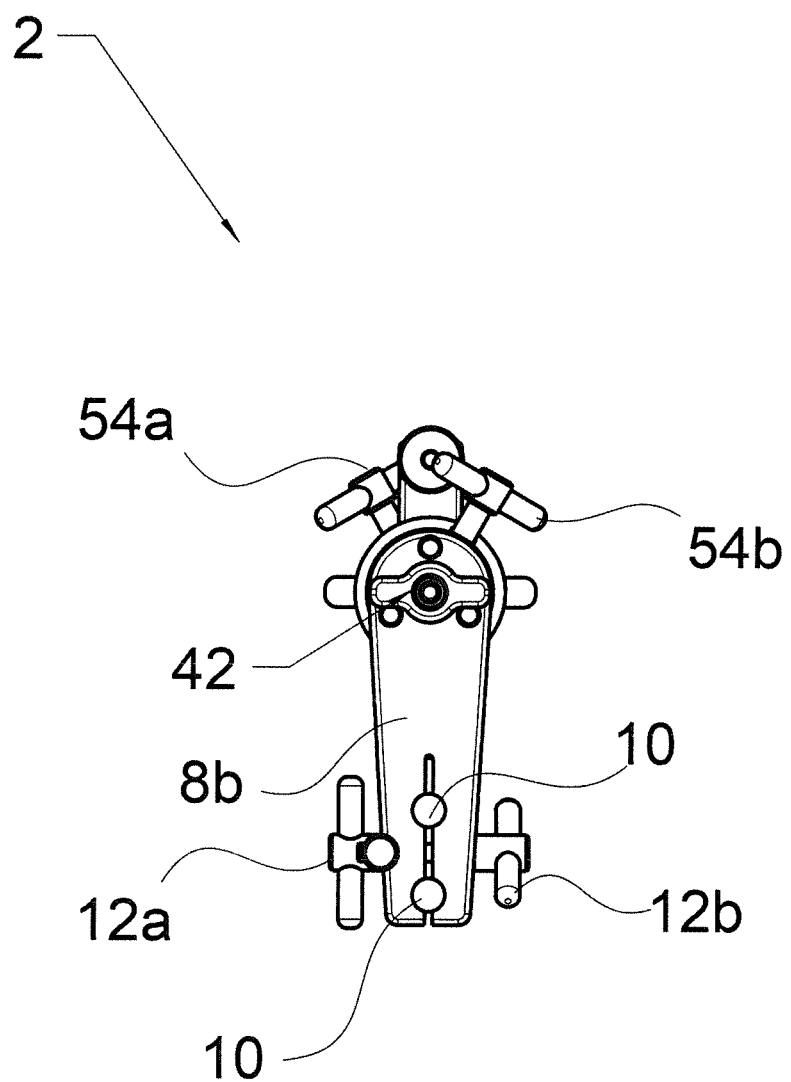
FIG. 2B shows the embodiment of FIGS. 1A-2A in a view at the second carriage along the longitudinal direction of the device in an opposite direction as compared to FIG. 2A.
Figure 2C:
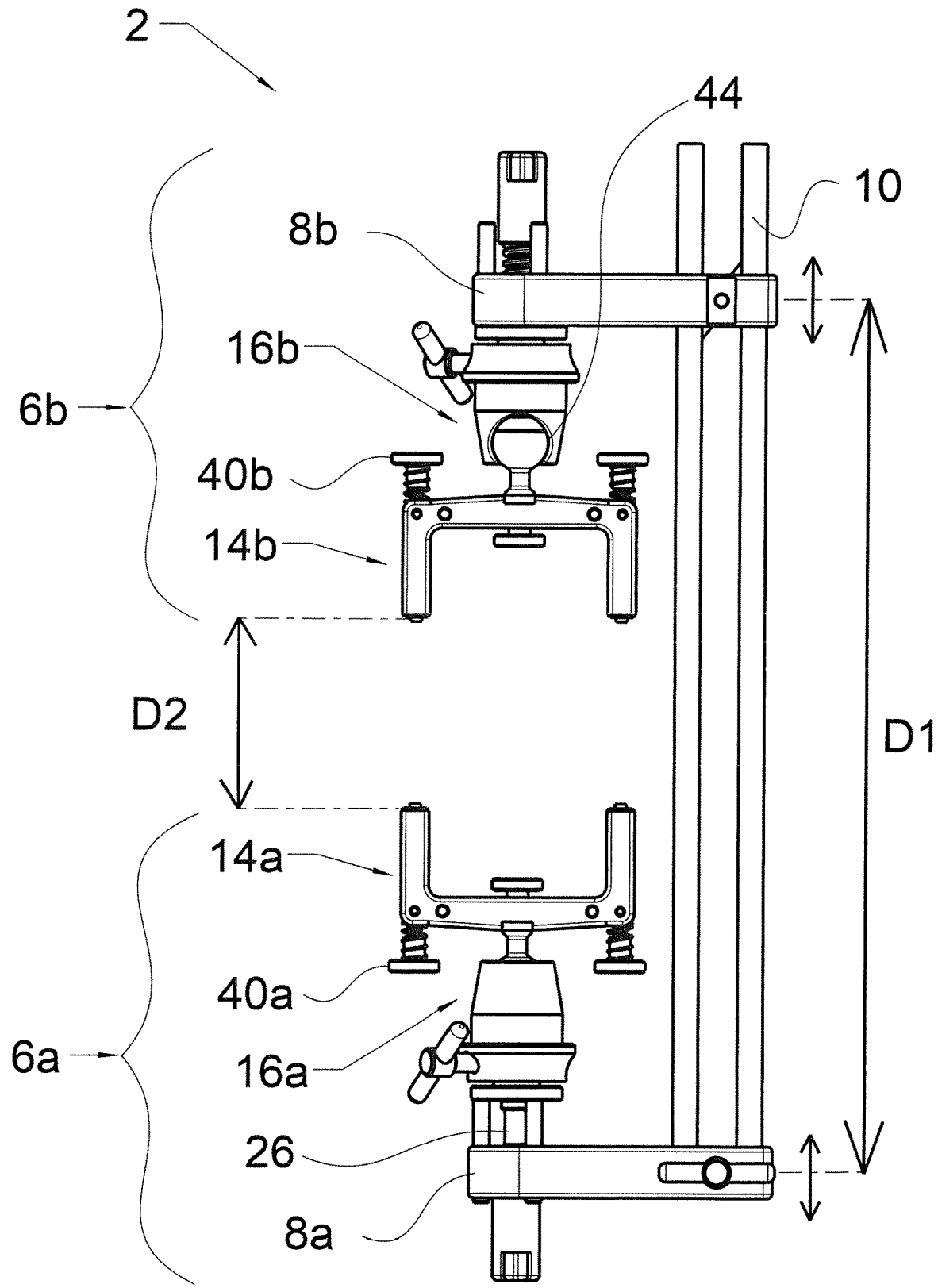
FIG. 2C shows the embodiment of FIG. 1A-2B in a view along a vertical direction perpendicular to the longitudinal direction of the device.
Figure 2D:
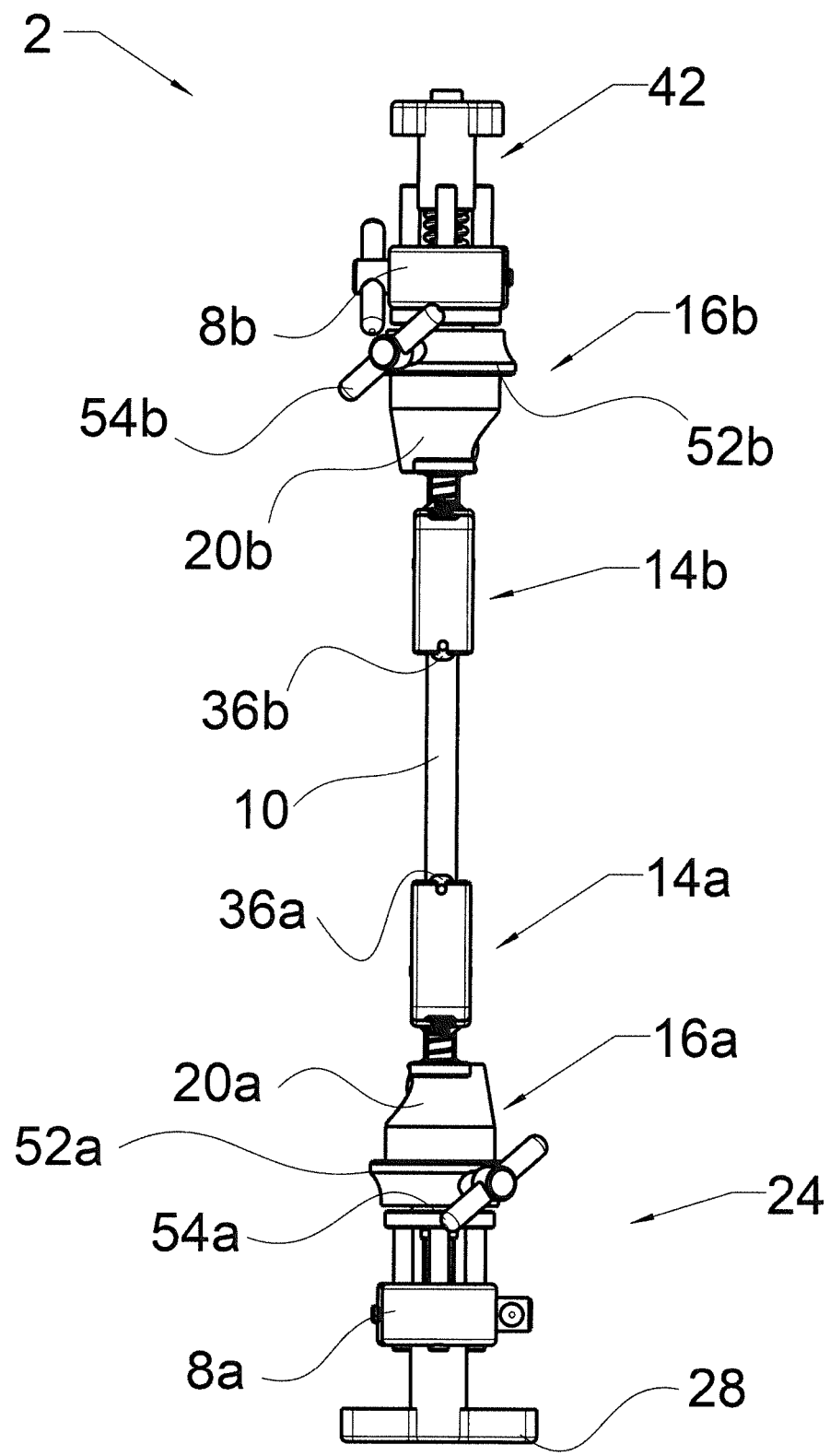
FIG. 2D shows the embodiment of FIG. 1A-2C in a view along the width direction perpendicular to the longitudinal direction of the device and the vertical direction.
Figure 2E:
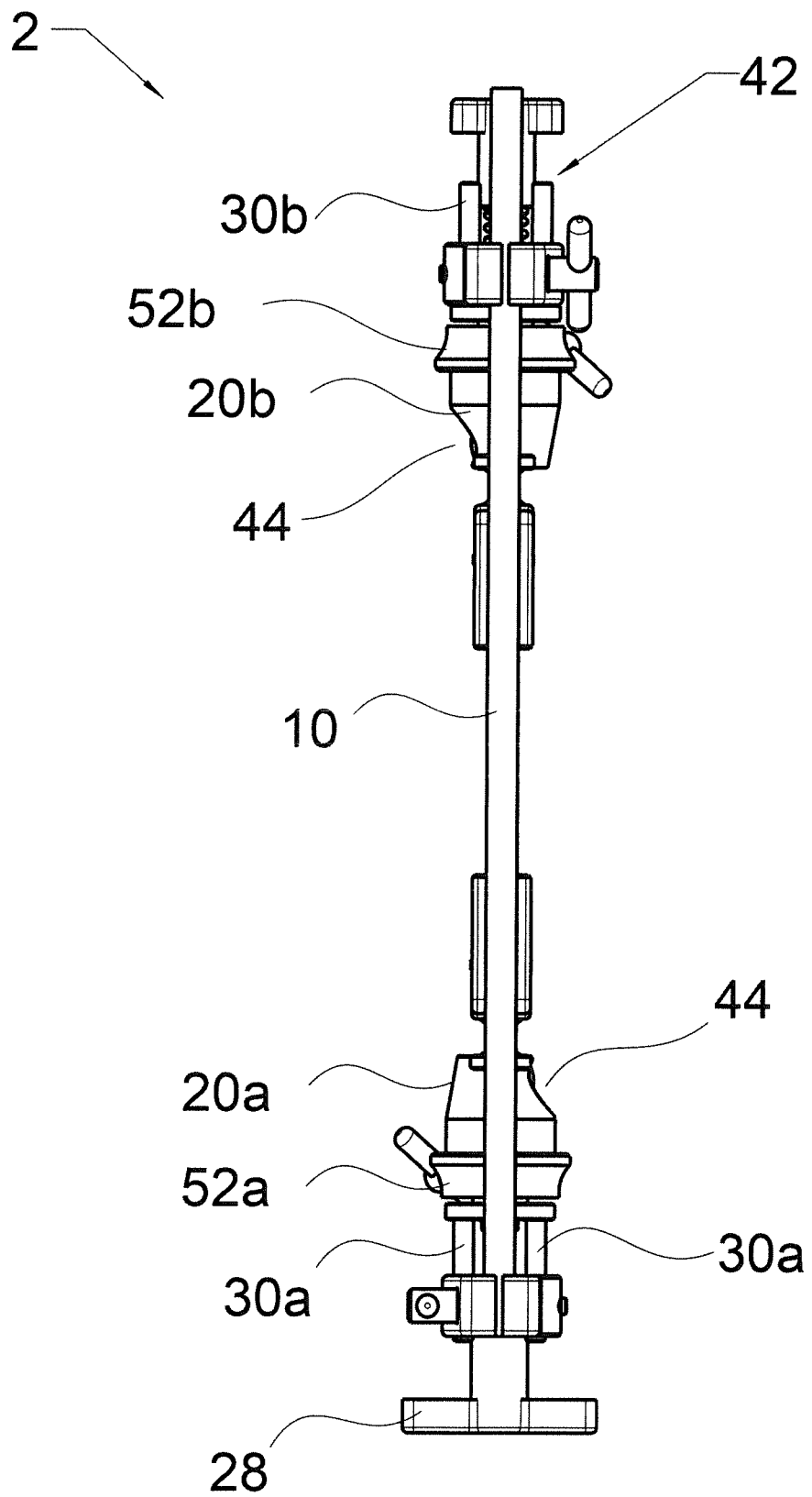
FIG. 2E shows the embodiment of FIG. 1A-2D in a view along the width direction of the device in an opposite direction as compared to FIG. 2D.

At least one of the support members 14a, 14b, preferably (and as shown in the Figures) both support members 14a, 14b are coupled to the corresponding carriage 8a, 8b via a respective spherical joint 16a, 16b (see FIG. 2C). In the embodiment shown in the Figures, the balls 18a, 18b of the spherical joints are coupled to the support members 14a, 14b, while the sockets 20a, 20b of the spherical joints 16a, 16b are coupled to the carriages 8a, 8b. However, this arrangement may be vice versa for one/all spherical joint/s. Coupling of the ball 18a, 18b to the support member 14a, 14b may be accomplished by any suitable means. In the embodiment of the Figures, the balls 18a, 18b are coupled to the corresponding support members 14a, 14b by means of a respective screw 22, particularly a nut 22.

The coupling of the support member 14a, 14b to the carriage 8a, 8b via the spherical joint 16a, 16b allows for an adjustment of the orientation of the support member 14a, 14b relative to the respective counterpart of the spherical joint 16a, 16b (socket 20a, 20b) and thus the respective carriage 8a, 8b, and thus via the base frame 10 also relative to the other carriage assembly 6a, 6b with the other support member 14a, 14b.

The first carriage assembly 6a (see FIG. 2C; shown to the left in FIGS. 1A, 1B and to the bottom in FIGS. 2C-2E) may comprise an extension assembly 24 configured for adjusting a distance D2 between the first and second support members 14a, 14b and thus the first and second pins 4a, 4b. The extension assembly 24 may comprise any suitable mechanism. For example, the extension assembly 24 may include a threaded rod 26 and an extension screw 28 mounted on the threaded rod. The threaded rod 26 may be coupled to the socket 20 of the spherical joint 16a. The socket 20a of the spherical joint 16a may be further coupled to at least one, preferably at least two, more preferably at least three guide rods 30. The carriage 8a may comprise a corresponding number of seats, particularly holes, particularly through holes, for receiving the guide rods 30.

The extension assembly 24 may be configured such that actuating the extension screw 28 results in a longitudinal movement of the socket 20a and thus the support member 14a and the pin 4a relative to the base frame 10. The direction of the movement may depend on the rotating direction of the screw 28. The longitudinal movement of the socket 20a may be achieved, e.g., by having the extension screw 28 and the socket 20a on opposing sides of the carriage 8a with the threaded rod 26 traversing the carriage 8a. In this configuration, the carriage 8a acts as a screw fence 32 for the extension screw 28. The threaded hole that forms the counterpart to the threaded rod 26 and translates the rotational movement of the extension screw 28 into a longitudinal movement of the socket 20a may be located in any suitable member. For example, it may be located in the extension screw 28 or in the carriage 8a.

The extension assembly 24 may comprise a locking mechanism (not shown) that may be configured for preventing a longitudinal movement of the support member 14a. In the embodiment shown in the figures, the locking mechanism may prevent a rotation of the extension screw 28. This can be achieved by the interaction of the pitch of the threaded rod 26 and the extension screw 28 to generate a self-blocking thread. Alternatively any mechanism to increase friction within the system of the extension assembly 24 may be suitable to achieve a locking mechanism.

The support members 14a, 14b may be configured for mounting the respective pin 4a, 4b. Preferably, the support members 14a, 14b are configured for mounting the respective pin 4a, 4b at two mounting sites, although other numbers of mounting sites are also contemplated. The attachment of the pin 4a, 4b at the mounting sites may be implemented in any suitable way. For example, the support member 14a, 14b may comprise a bracket 36 at each mounting site, i.e. two brackets 36 for each support member 14a, 14b in the embodiment shown in the Figures. Each bracket 36 may be configured for clamping the respective pin 4a, 4b at the respective mounting site. Preferably, each bracket 36 is coupled to a bracket spring 38 and a bracket screw 40. The bracket spring 38 may be configured for securing the bracket 36 to the support member, while still allowing the bracket 36 to be opened far enough to insert the pin 4a, 4b. Preferably, the bracket spring 38 biases the bracket 36 to a closed position and the bracket 36 may be brought into an open position for inserting the pin 4a, 4b by actuating the spring, e.g., by pushing the bracket screw 40 towards the support member 14a, 14b.

With this configuration, the support member 14a, 14b may be loosely mounted to the pin 4a, 4b in a way that still allows for a movement of the support member 14a, 14b in the mounting site but prevents the support member 14a, 14b from unintentionally falling off the pin 4a, 4b. After this initial loose attachment, the support member 14a, 14b may be fixed in its final position by actuating the bracket screw 40. The bracket screw 40 may be configured for tightening the bracket 36, which may result in the support member 14a, 14b being fixedly clamped to the pin 4a, 4b through the bracket 36. In this way, the risk of dropping the support member 14a, 14b during the procedure of attachment to the pin 4a, 4b is significantly reduced. This is particularly relevant for medical applications, such as the medical applications of the positioning device of the present invention, in which dropping of a device such as the support member 14a, 14b may result in severe consequences for the patient. Moreover, the above mounting mechanism provides for a flexible and comfortable mounting of the support member 14a, 14b to the pin 4a, 4b, as the support member 14a, 14b may be first attached at the first mounting site and then attached at a second mounting site. Throughout the attachment procedure, the pin 4a, 4b may be repositioned relative to the support member 14a, 14b, thus providing for optimal positioning of the pin 4a, 4b relative to the support member 14a, 14b.

Preferably, the support member may apply a pretension to the pin 4a, 4b, when the pin 4a, 4b is fixed via the brackets 36 by the described three point fixation. Applying pretension to the pin 4a, 4b makes the pin 4a, 4b more stable during the procedure of repositioning.

Preferably, the bracket's position on the support member may be adjustable. For example, the support member may comprise a movable mount (not explicitly shown in the Figures) that comprises the bracket. The mount may be configured to be fixed in different positions relative to the support member 14a, 14b.

According to the invention, the second carriage assembly 6b may be identical to the first carriage assembly 6a. Alternatively, the second carriage assembly 6a may not comprise the extension assembly 24. Instead, the support member 14b may be coupled to the carriage 8b, either directly (resulting in a fixed coupling) or via spherical joint 16b, which enables a rotational movement but no longitudinal movement.

Additionally or alternatively, one of the carriage assemblies 6a, 6b may comprise a force sensor 42 (dynamometer), configured for measuring an applied force. The force sensor 42 may be of any suitable type, e.g., one of the force sensors already mentioned. For example, the force sensor 42 may use the principle of a spring balance. For example, the force sensor 42 may comprise a spring and a corresponding scale on, e.g., one or more of the corresponding guiding rods 30. If a longitudinal force is applied on the corresponding pin 4a, 4b, the spring is extended (or contracted) proportional to the applied force in accordance with Hook's Law and this expansion is displayed to the user by the corresponding scale, which translates the expansion of the spring into the corresponding amount of force.

Figure 3:
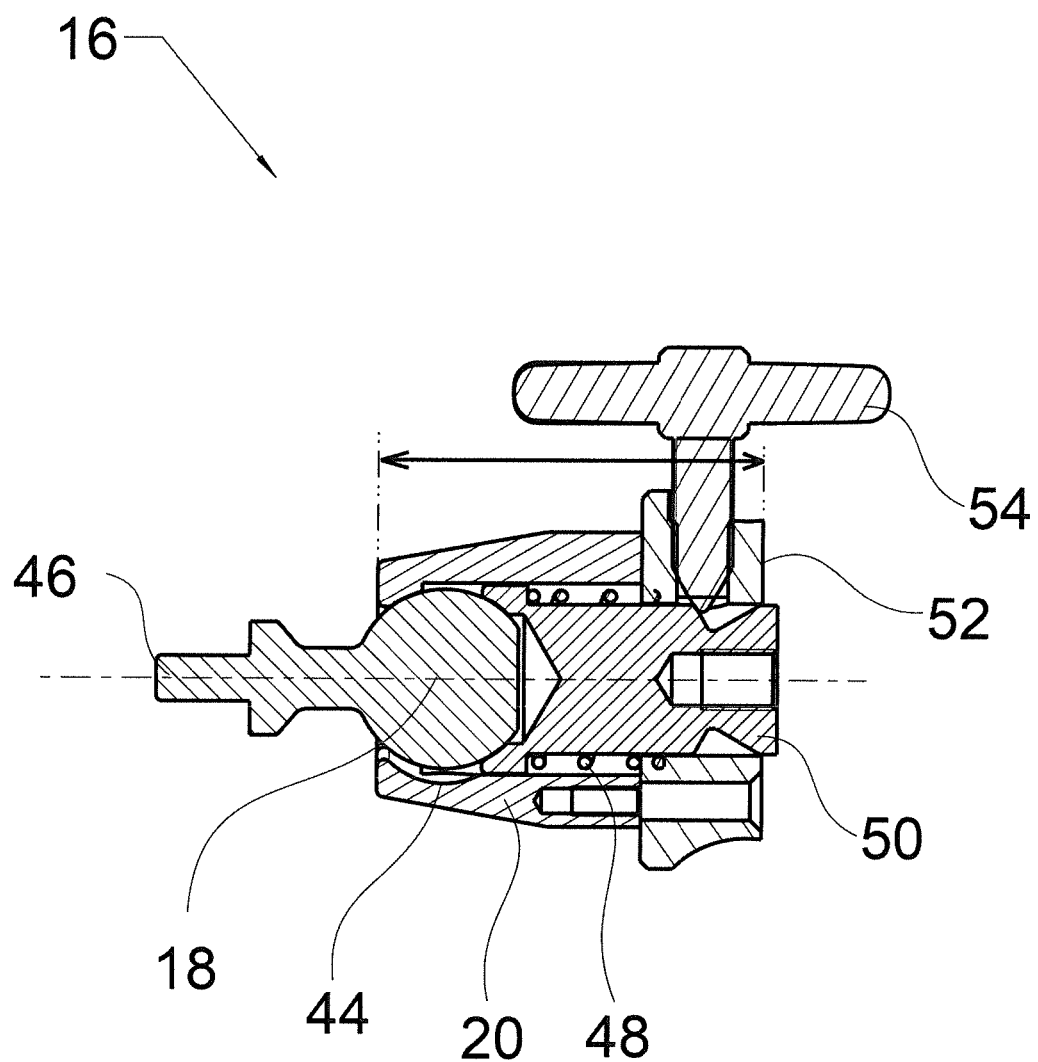
FIG. 3 shows a cross section through a spherical joint.

Any suitable spherical joint may be used in the invention. However, FIG. 3 shows a cut through a preferred embodiment of the spherical joint 16 including ball 18 and socket 20 according to the invention. The socket 20 is configured for receiving the ball 18. The ball 18 may be inserted into the socket 20 through a side opening 44. The ball 18 may comprise a shaft 46 that extends from the ball 18 and that is configured for being attached to the appropriate member, preferably the support member 14. Note that the ball 18 with the shaft 46 may also be configured for attachment to the carriage 8 and/or the extension rod 26. The spherical joint 16 may comprise a joint locking mechanism. The joint locking mechanism serves for locking the ball 18 in the socket 20 when in the closing position and for allowing the ball 18 to leave the socket 20 when in an opening position.

The exemplary and inventive joint locking mechanisms shown in the Figures, and particularly in FIG. 3, comprises a joint spring 48, a sleeve 50, a locking ring 52 and a joint screw 54. In a preferred embodiment as shown in FIG. 3, the locking ring 52 is coupled to the socket 20. This coupling may be implemented by any suitable means, for example, one or more threading, screws, nails, rivets, clamps and/or welds and/or the like. The locking ring—socket—assembly is arranged surrounding the sleeve 50 and movable relative to the sleeve 50 as indicated by the double arrow in FIG. 3. If the locking ring—socket—assembly is in the closing position, the sleeve 50 blocks the opening 44 of the socket 20, thus preventing the ball 18 from leaving the socket 20 through opening 44. If the locking ring—socket—assembly is, however, in the opening position, the sleeve 50 does not block the opening 44, thus allowing the ball 18 to leave the socket 20 through opening 44. The locking spring 48 may be configured for biasing the locking assembly into the closing position. Thus, a force needs to be applied in order to switch the locking ring—socket—assembly into the opening position to enable the ball 18 to escape the socket 20. This advantageously provides for a security mechanism.

The joint locking mechanism may comprise a joint screw 54 for locking the locking ring 52 with the sleeve 50, thus inhibiting a movement of the locking ring—socket—assembly into the opening position.

According to a preferred embodiment and as shown in the Figures, the medical positioning device is constructed such that the pins do not interfere with the base frame.

Preferably, the base frame defines an area and/or a volume that is at least partially surrounded by the base frame and that is free of the pins. In the case of the preferred embodiment shown in the Figures, the two rods of the base frame 10 define an area A between them. This area A is free of the pins 4a, 4b when the medical positioning device is coupled to the pins 4a, 4b. This provides the advantage that the medical positioning device may be comfortably arranged around the body portion to be treated without the problem of taking care that the base frame actually fits around the body portion. Furthermore, the medical positioning device may be attached to and removed from the pins and thus the body without the necessity of disassembling the medical positioning device.

Figure 1B:
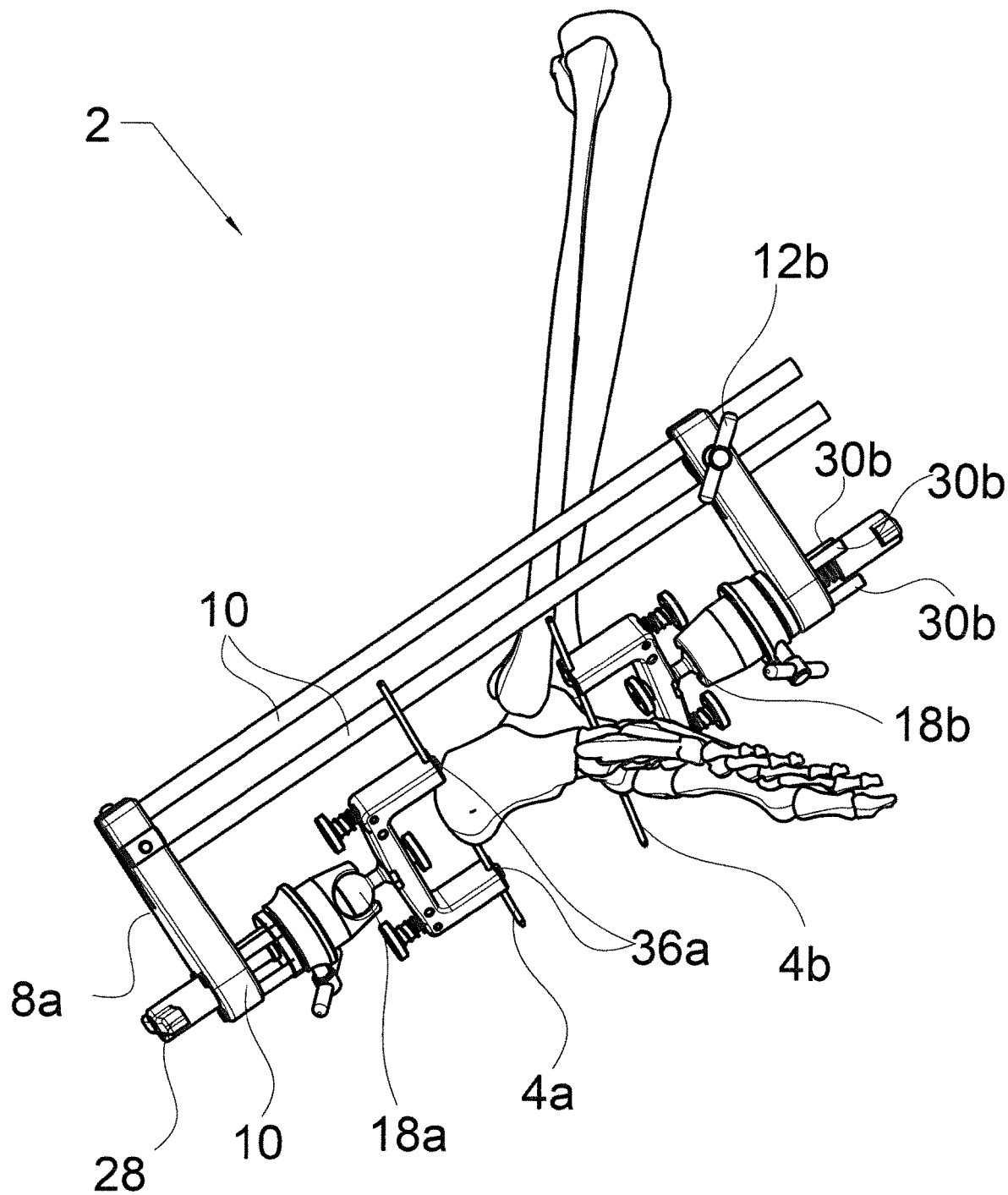
FIG. 1B shows the medical positioning device of FIG. 1A in the same view, but attached to a human's foot.

Preferably, the pins 4a, 4b are configured for traversing a patient's body part. Preferably, the mounting sites are configured to be located on different sides of the traversed body part. For example, the pins 4a, 4b may be configured for traversing a human's foot. For example, the first pin 4a may be configured for traversing the Calcaneus and the second pin 4b may be configured for traversing the Talus, e.g., as shown in FIG. 1B, or vice versa. In the case shown in FIG. 1B, first mounting sites of the pins 4a, 4b are located on a lateral side of the foot and second mounting points of the pins 4a, 4b are located on a medial side of the foot.

The preferred embodiment as described above may be used according to the following method.

In general, a preferred embodiment of the invention is very flexible in terms of the attachment procedure, i.e. the procedure of attaching the medical positioning device to a patient. This enables a user to use the medical positioning device for many different specific applications such as different body parts of different types of patients. A user, e.g. a physician, may start with assembling the complete medical positioning device from its individual members and then attach the completely assembled medical positioning device to pins in the patient's body portion to be repositioned. Alternatively, the user may assemble the medical positioning device on site, i.e. the user only pre-assembles none, one or more parts of the medical positioning device and assembles these (pre-assembled) parts, e.g. one after the other, to the pins and/or those parts of the device that have already been assembled to the pins.

Referring again to the preferred embodiment shown in the Figures, a user may preferably attach first and second pins 4a, 4b to a patient's body as required from a medical point of view. The user may then assemble the first and second support members 14a, 14b to the first and second pins 4a, 4b, respectively. The support members 14a, 14b may already have the balls 16a, 16b coupled to them or the user may now couple the balls 16a, 16b to the support members 14a, 14b. The user may couple the first socket 20a to the first ball 16a of the first support member 14a and the second socket 20b to the second ball 16b of the second support member 14b. The user may then attach the first carriage 8a to the first spherical joint 16a, i.e., the first socket 20a, and the second carriage 8b to the second spherical joint 16b, i.e., the second socket 20b. Alternatively, the user may pre-assemble the carriage 8a, 8b with the socket 20a, 20b and assemble the carriage—socket—assembly as one piece to the ball 16a, 16b. In any case, the user may then couple the first and second carriages 8a, 8b with the base frame 10. This procedure will automatically result in the first and second carriages 8a, 8b having the correct distance D1. Alternatively, the user may pre-assemble the base frame 10 with one or both of the carriages 8a, 8b and optionally one or both of the sockets 20a, 20b.

With the device 2 attached to the pins 4a, 4b through the patient's body, the user may then actuate the extension member 24, e.g., the extension screw 28, thus causing the carriage assemblies 6a, 6b (and thus the pins 4a, 4b) to move away from each other. Thereby, the body parts of the patients are repositioned according to the actuation of the extension screw 28.

In a further alternative, the user may even pre-assemble the base frame 10 with one or both of the carriages 8a, 8b, optionally one or both of the sockets 20a, 20b, optionally one or both of the balls 16a, 16b, and optionally one or both of the support members 14a, 14b. In this case, the user may set the distance D1 to an appropriate value upon coupling the medical positioning device to the pins 4a, 4b.

In a preferred embodiment, the base frame 10 may be, directly or indirectly, coupled to a fix member that is fixedly installed, such as an operation table, a wall, a floor, a ceiling and the like. In the case of an indirect coupling to the fix member, any suitable intermediate fixation device may be used, e.g., a flexible mounting arm for surgical devices. This provides additional stability to the system.

A person skilled in the art will recognize that the specific sequence of assembling the individual components of the medical positioning device may vary depending on the specific application of the device.

Figure 4:
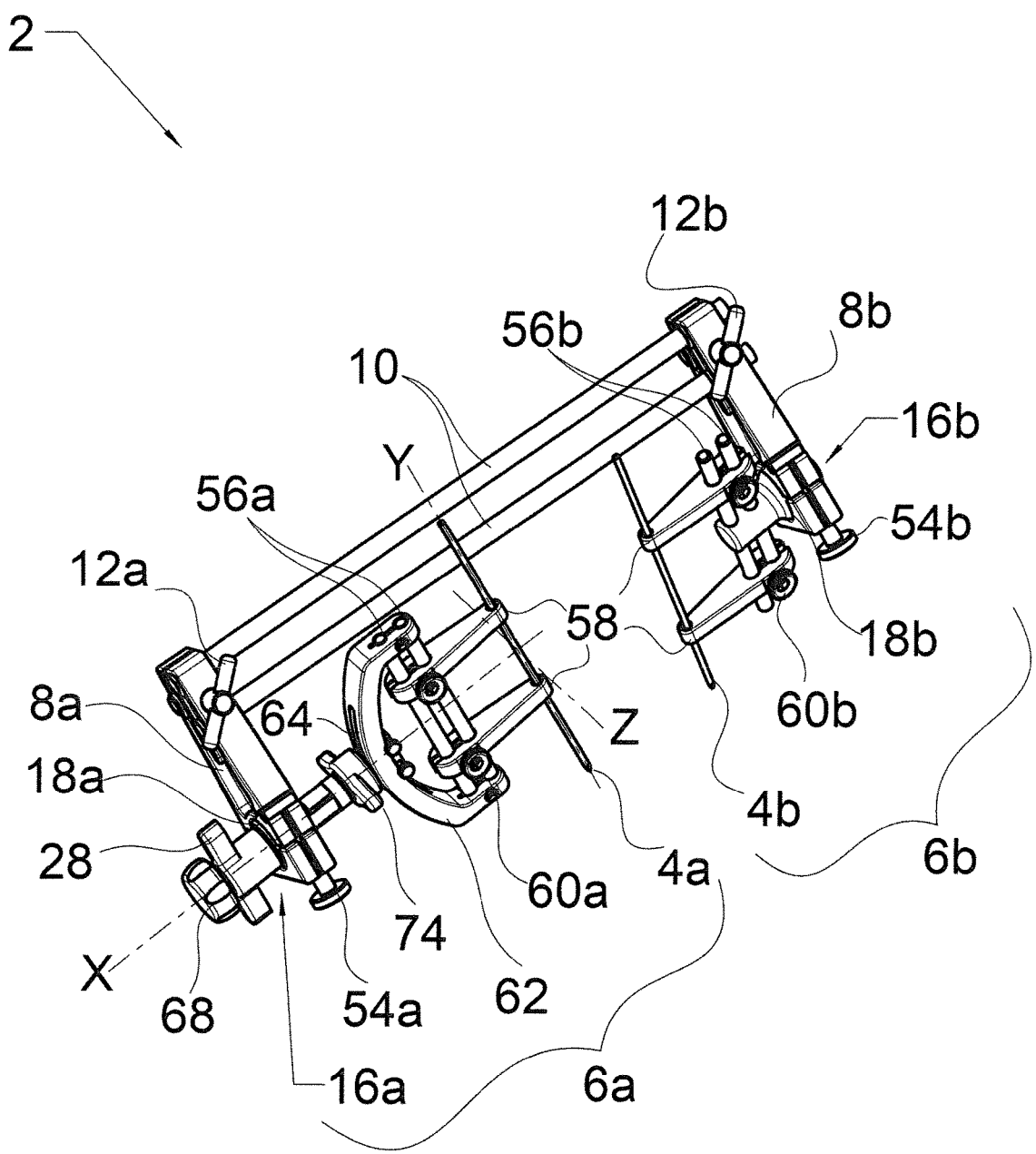
FIG. 4 shows a perspective view of another embodiment of the medical positioning device.
Figure 5:
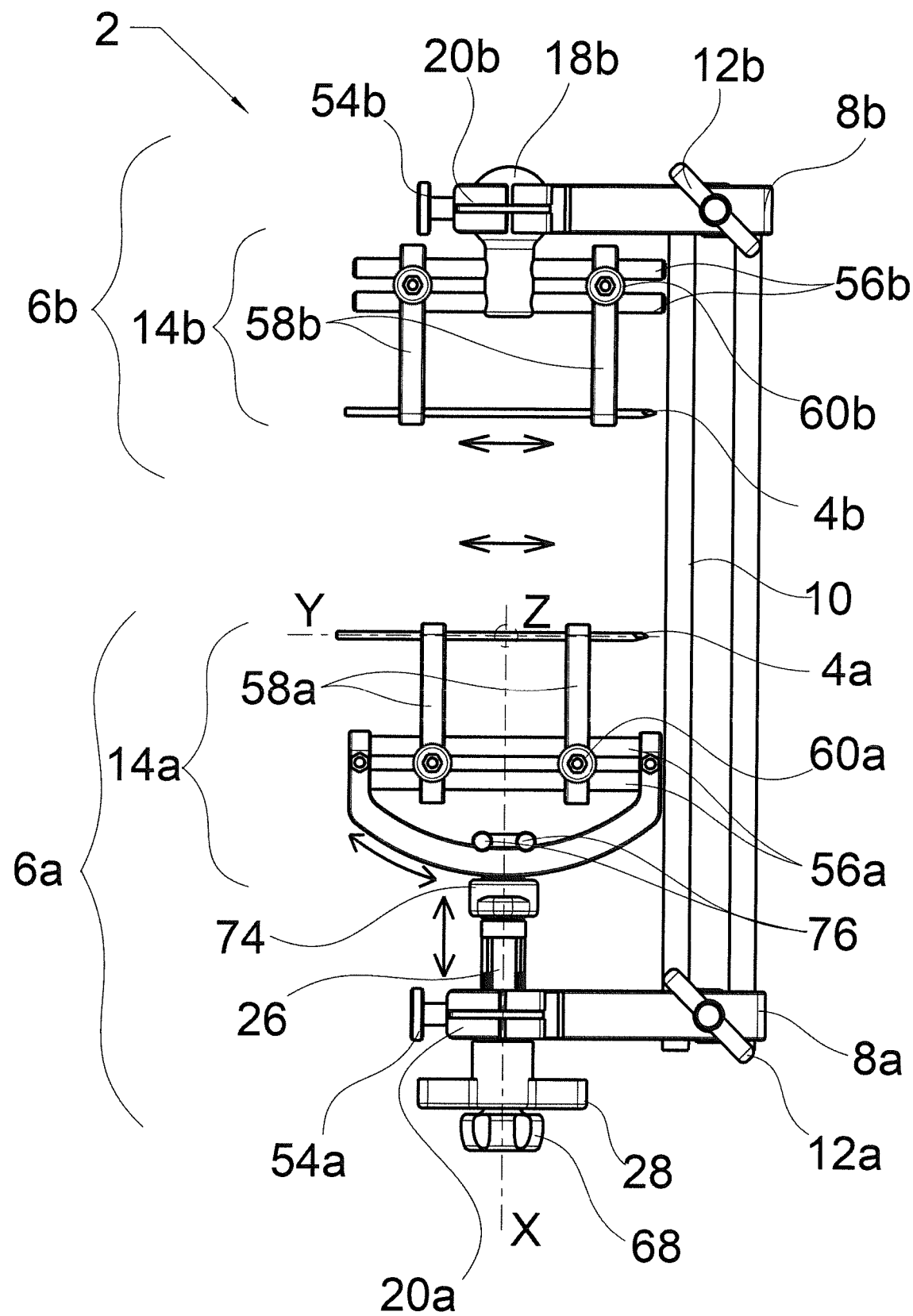
FIG. 5 shows the embodiment of FIG. 4 in a side view.

FIG. 4 shows another preferred embodiment of a medical positioning device 2 according to the present invention in a perspective view. FIG. 5 shows the embodiment of FIG. 4 in a side view along the width direction of the medical positioning device 2. FIGS. 4 and 5 show two alternative carriage assemblies 6a, 6b, each of which is exchangeable with the carriage assemblies 6a, 6b described above. The medical positioning device 2 of FIGS. 4 and 5 allows for the adjustment of the pin positions via spherical joints as well as a longitudinal distraction, as described above with the previous embodiments. In addition, it may provide for an additional independent rotational correction of at least one of the pins about at least one, or optionally two rotation axes.

The medical positioning device 2 is shown with first and second pins 4a, 4b coupled to first and second carriage assemblies 6a, 6b, respectively. Again, each carriage assembly 6a, 6b may comprise a carriage 8a, 8b configured for coupling to a base frame 10 and a support member 14a, 14b for mounting the respective pin 4a, 4b, for example as described above in the context of other embodiments. For example, the pins 4a, 4b may be mounted via brackets (not shown).

The first and second carriage assemblies 6a, 6b may each comprise a spherical joint 16a, 16b, as shown in FIGS. 4-6D. Each spherical joint 16a, 16b may comprise a ball 18a, 18b and a corresponding socket 20a, 20b. The socket 20a, 20b is a part of and/or attached to the corresponding carriage 8a, 8b, and the ball 18a, 18b is attached to the corresponding support member 14a, 14b. The socket 20a, 20b may comprise two socket clamps, which are connected by a hinge. In a closed position, the socket clamps are configured for clamping the corresponding ball 18a, 18b, whereas in an open position, the ball may be removed from the socket. The shown spherical joint 16a, 16b also comprises a joint screw 54a, 54b configured for locking the ball 18a, 18b within the closed socket clamps in a desired position. Hence, if the joint screw 54a, 54b is loosened, the ball 18a, 18b of the spherical joint may be moved, i.e. rotated, with respect to the socket 18a, 18b. If the joint screw 54a, 54b is tightened, the orientation of the ball 18a, 18b relative to the socket 20a, 20b is fixed. This provides for the possibility of orienting the corresponding pin 4a, 4b by appropriately orienting the position of the ball 18a, 18b relative to the socket 20a, 20b.

FIGS. 4 and 5 show a preferred support member 14b in the upper (right) part of the Figures. In the shown embodiment, the support member 14b comprises two support rods 56b. However, it is also possible that the support member 14b only comprises one support rod 56b or more than two support rods 56b. The support rods 56b are attached to an extension of the ball 18b of the spherical joint 16b and preferably run parallel. Two support arms 58b are movably attached to the support rods 56b. Each support arm 58b provides a mounting site for the respective pin 4b. Each mounting site may be configured as already described above, i.e. with a bracket for attachment of the pin 4. Preferably, however, each support anti is configured to receive the corresponding pin 4 and to hold it via friction. Each support arm 58b comprises a support screw 60b. If the support screw 60b is loosened, the respective support arm 58b may be moved along the support rods 56b. Thus, the distance between the support arms 58b may be adjusted in order to provide sufficient space in between them for the body part to be treated. If the support screw 60b is tightened, the respective support arm 58b is fixed to the support rods 56b and may no longer be moved. The support member 14b of FIGS. 4 and 5 may also be combined with any of the other carriage assemblies 6.

FIGS. 4, 5, 6D and 7 show another preferred embodiment of a carriage assembly 6a in the lower (left) part of the Figures. This carriage assembly 6a comprises an alternative support member 14a. Alternative support member 14a comprises support arms 58a, which are mounted to support rods 56a by means of support screws 60a, as described for support member 14b above. However, the support rods 56a are not mounted to an extension of the ball 18a of the spherical joint 16a. Instead, the support rods 56a are mounted to a support frame 62. The support frame 62, and thus the support member 14a, is mounted to an extension assembly 24. The extension assembly 24 enables an adjustment of the position and/or orientation of the support member 14a, and thus the pin 4a, relative to the base frame 10, the second support member 14b and the pin 4b. As already mentioned above, the extension assembly 24 and/or the support member 14a may enable a longitudinal movement of the support member 14a and thus the pin 4a along the longitudinal axis X (see FIG. 4) of the medical positioning device 2. Additionally, they may enable a rotation of the support member 14a about at least one, or optionally about two axes of the medical positioning device 2. For example, the extension assembly 24 in combination with the support member 14a may enable a rotation about the longitudinal axis X and/or about a transversal axis Z (see FIG. 4) that is perpendicular to the longitudinal axis X. Preferably, the longitudinal movement as well as the one or two rotational movements may occur independently from one another.

In order to provide for a movement of the support member 14a along the longitudinal axis X, the extension assembly 24 may comprise an extension screw 28 mounted on a corresponding threaded rod 26. The extension assembly 24 may be configured such that actuating the extension screw 28 results in a longitudinal movement of the extension screw 28 relative to the threaded rod 26 and thus in a longitudinal movement of the support member 14a. For example, the extension screw 28 may use the ball 18a as a fence while the threaded rod 26 may be engaged with the ball 18a, which prevents a rotation of the threaded rod 26 upon actuation of the extension screw 28 and instead results in the longitudinal movement.

In order to provide for a rotation of the pin 4a about the longitudinal axis X, the support member 14a may be mounted on a rotation assembly 65. The rotation assembly may comprise a rotation rod 66. The rotation rod 66 may extend through the extension screw 28 and the threaded rod 26. The rotation assembly 65 may comprise a longitudinal fixation element 68 (see FIG. 7, which shows a longitudinal cut through carriage assembly 6a of FIGS. 4-6D). The longitudinal fixation element 68 may be configured for allowing the rotation of the rotation rod 66 about the longitudinal axis X when in an open state and for inhibiting the rotation of the rotation rod 66 about the longitudinal axis X when in a closed state.

For example, this may be achieved with a tooth system that is configured for engagement upon closing the fixation element 68 and for disengagement upon opening the fixation element 68. For instance, the threaded rod 26 may comprise a first set of teeth and a counterpart, for example a sliding carriage 64 attached to the support member 14a, comprises a corresponding second set of teeth. The rotation rod 66 may extend through the extension screw 26 and into the counterpart 64. The counterpart 64 may be a part of the rotation assembly 65. In addition, the rotation rod 66 and the counterpart (here sliding carriage 64) may be connected via a thread. By turning the rotation rod 66 via actuation of the fixation element 68 the thread is adjusting the distance between the threaded rod 26 and the counterpart 64, and consequently between the first and second sets of teeth. If the rotation rod 66 is tightened by closing the fixation element 68, the first and second sets of teeth are fully engaged and the rotation of the support member 14a about the longitudinal axis X is blocked. If the fixation element 68 is loose, the two sets of teeth are not engaged and the rotation of the support member 14a about the longitudinal axis X is free. Preferably, the longitudinal axis X crosses the pin 4a.

In order to provide for a rotation of the pin 4a about the transversal axis Z, any suitable mechanism is contemplated. For example, the support member 14a may have a support frame 62 with a pivot point. The pivot point is preferably located on the transversal axis Z and on the axis of the first pin 4a. In order to provide for a rotation of the pin 4a about the transversal axis Z, i.e. about the pivot point, the support member 14a may be mounted on the sliding carriage 64 via the support frame 62. For example, the support frame 62 may comprise a guidance 72, e.g. a slot, which engages with the sliding carriage 64 to provide for accurate rotational movement of the support member 14a. The sliding carriage 64 may comprise a clamping mechanism, which may include a screw 74 on a thread of the sliding carriage 64, preferably a nut 74, and a clamp 76. When the screw (here the nut) 74 is loosened, i.e. it is in an open state, the support frame 62 may move along the sliding carriage 64. Saying it the other way around, the sliding carriage 64 may move along the guidance 72 i.e. the support frame 62. Thus, when the support member 14a is in the desired orientation, the screw 74 may be brought into the closed position, which results in a fixation of the support member 14a. The fixation may, for example, be achieved by clamping the support frame 62 between the screw 74 and the clamp 76. The support frame 62 may have any suitable shape. Preferably, it has a C-shape, U-shape, V-shape or the like. However, most preferably, the support frame 62 has a form that corresponds to the way of sliding carriage 64 along the support frame 62, i.e. a curvilinear shape.

Preferably, the transversal axis Z crosses the pin 4a. Preferably, the longitudinal axis X and the transversal axis Z cross the pin 4a in the same point. In this case, the medical positioning device 2 not only provides for an individual and independent rotational correction of the orientation of the pin 4 about two axes. The two independent rotational movements also have the same center of rotation. Assuming correct installation of the medical positioning device 2 in the body part to be treated, the center of rotation is preferably located within the body part to be treated.

The application of the embodiment of the medical positioning device 2 of FIGS. 4 and 5 may occur according to the method described above. Nevertheless, further advantages will be explained by reference to FIGS. 6A-6D.

Figure 6A:
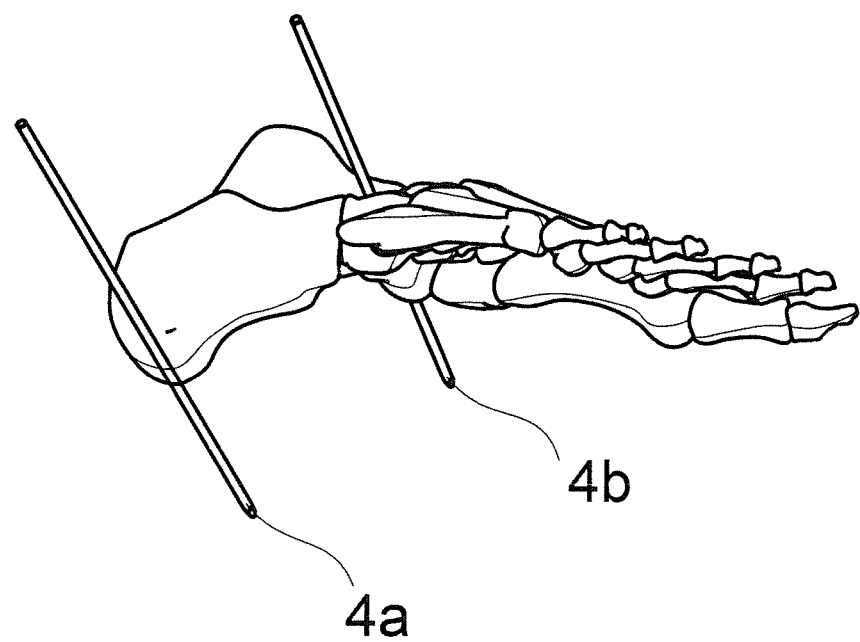
FIGS. 6A-6D show schematic illustrations of an application of the embodiment of FIGS. 4 and 5 in a sequence of four steps.
Figure 6B:
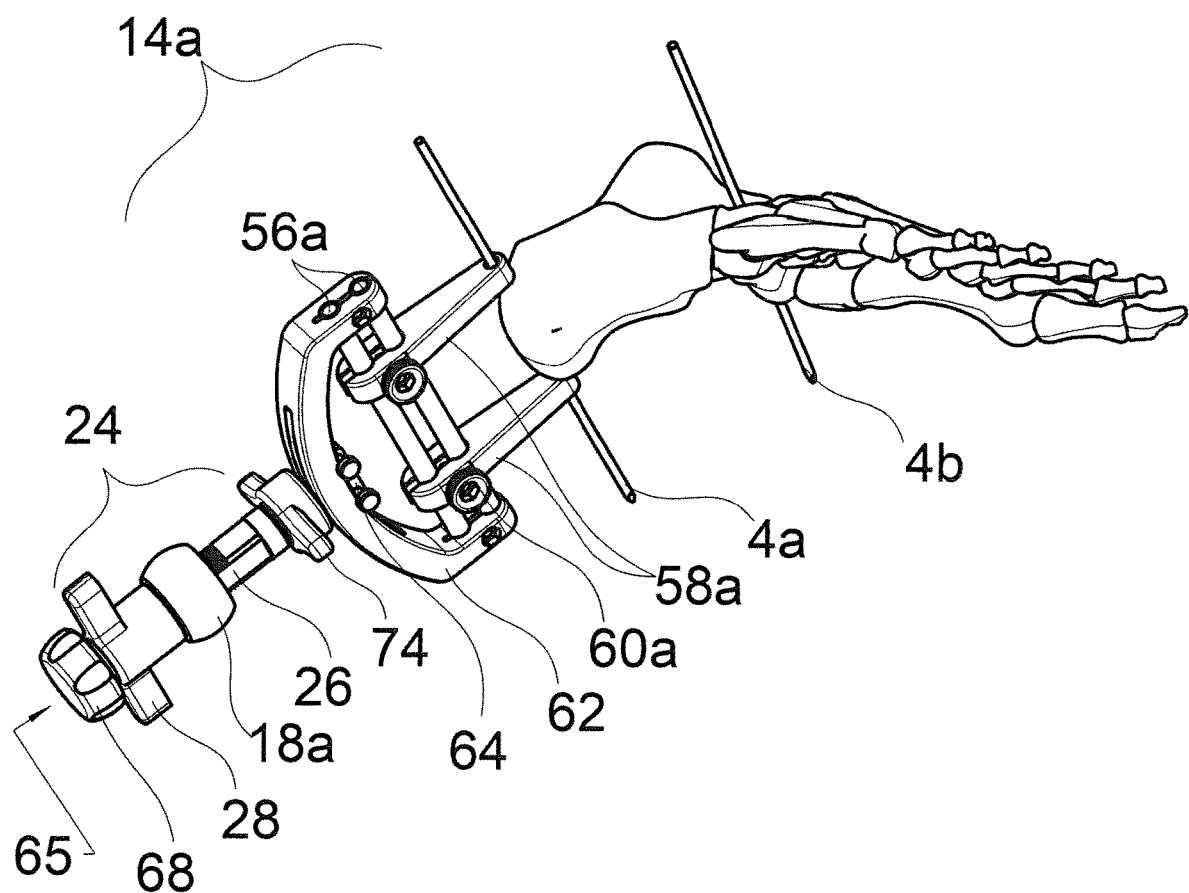
Figure 6C:
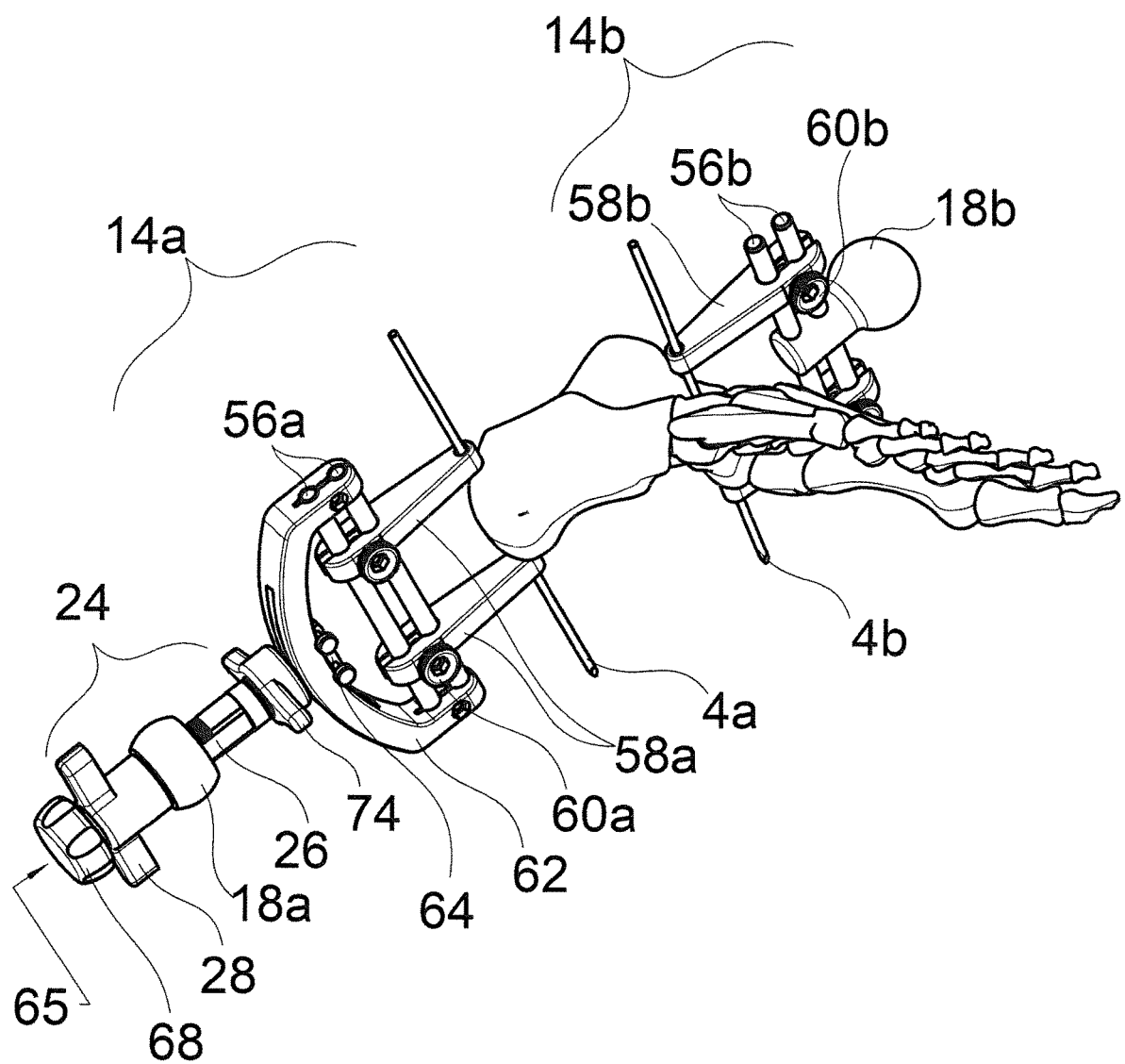

A user may preferably attach first and second pins 4a, 4b to a patient's body (here a human's foot) as required from a medical point of view (FIG. 6A). In FIG. 6A, the first pin 4a is applied to the rear, lower part of the calcaneus, while the second pin 4b is applied to the talus. The user may then assemble the first and second support members 14a, 14b to the first and second pins 4a, 4b, respectively (FIGS. 6B and 6C). The degree of pre-assemblage of the support members 14a, 14b depends on their specific configuration. For example, in the case of support member 14a of FIG. 6B, the support arms 58a may be individually attached to the pin 4a before the support arms 58a are mounted to the support rods 56a. Alternatively, the support arms 58a may first be mounted to the support rods 56a and afterwards attached to the pin 4a. In this case, the pin 4a must be selected to have an appropriate length in accordance with the length of the support rods 56a or shortened after installation in the body part to be treated.

In the case of support member 14b of FIG. 6C, the support rods 56b may be mounted on the extension of the ball 18 before the support arms 58b are mounted to the support rods 56b, and so on. The distance of the support arms 58 of each pin 4 may be adjusted to the widths of the calcaneus/talus by means of the support screws 60 as explained above. For example, the support arms 58 may be brought into contact with the skin of the respective body part. In this way, not only the pins may take hold of the foot but also the support arms 58. FIG. 6C shows the support member 14a including the extension member 24 attached to the first pin 4a. The extension member 24 also includes the ball 18a of the spherical joint 16a. However, the carriage 8a including the socket 20a has not yet been installed. FIG. 6C shows the support member 14b including the ball 18b of the respective spherical joint 16b attached to the pin 4b. The carriage 8b including the socket 20b has not yet been installed.

Figure 6D:
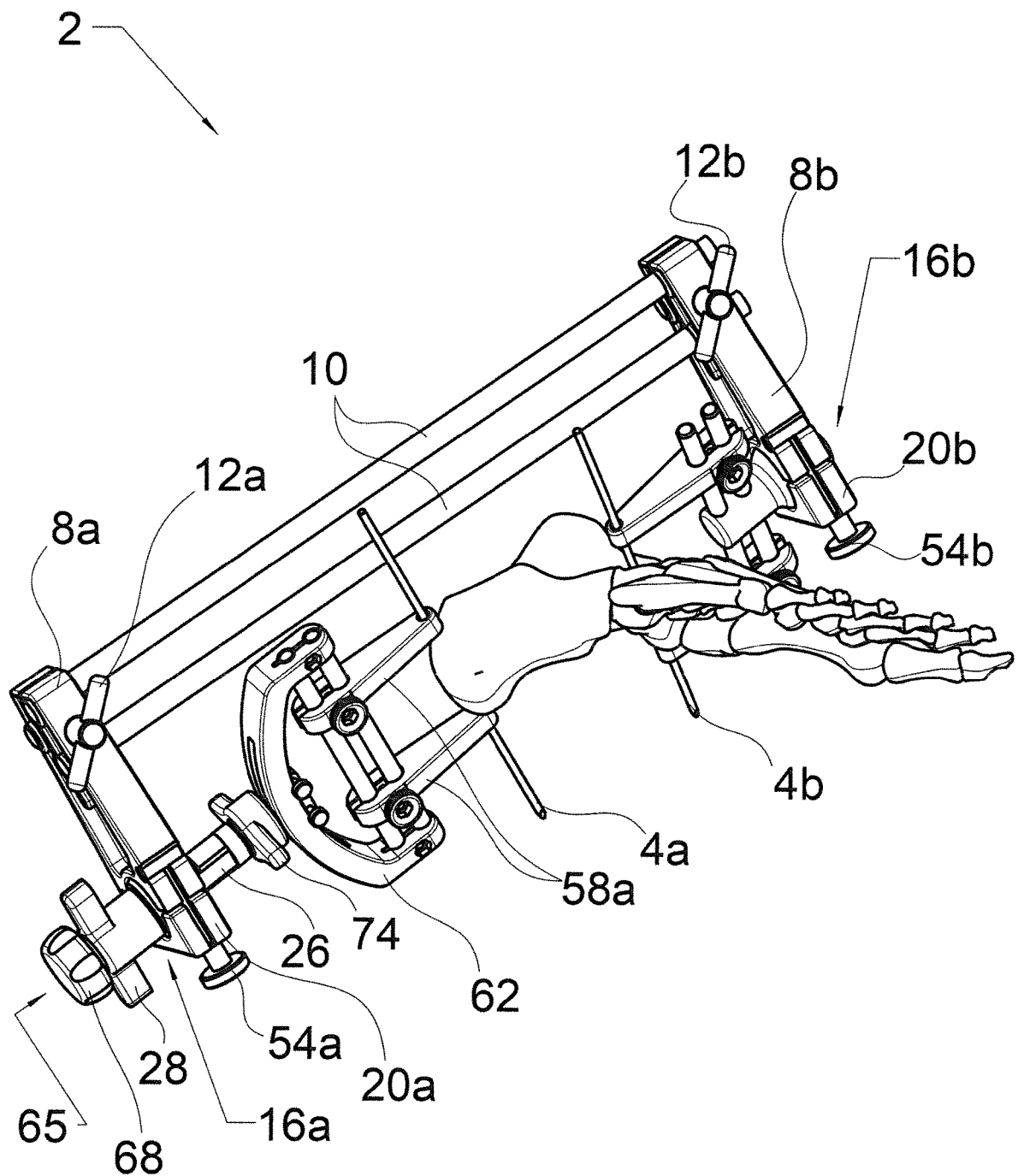
Figure 7:
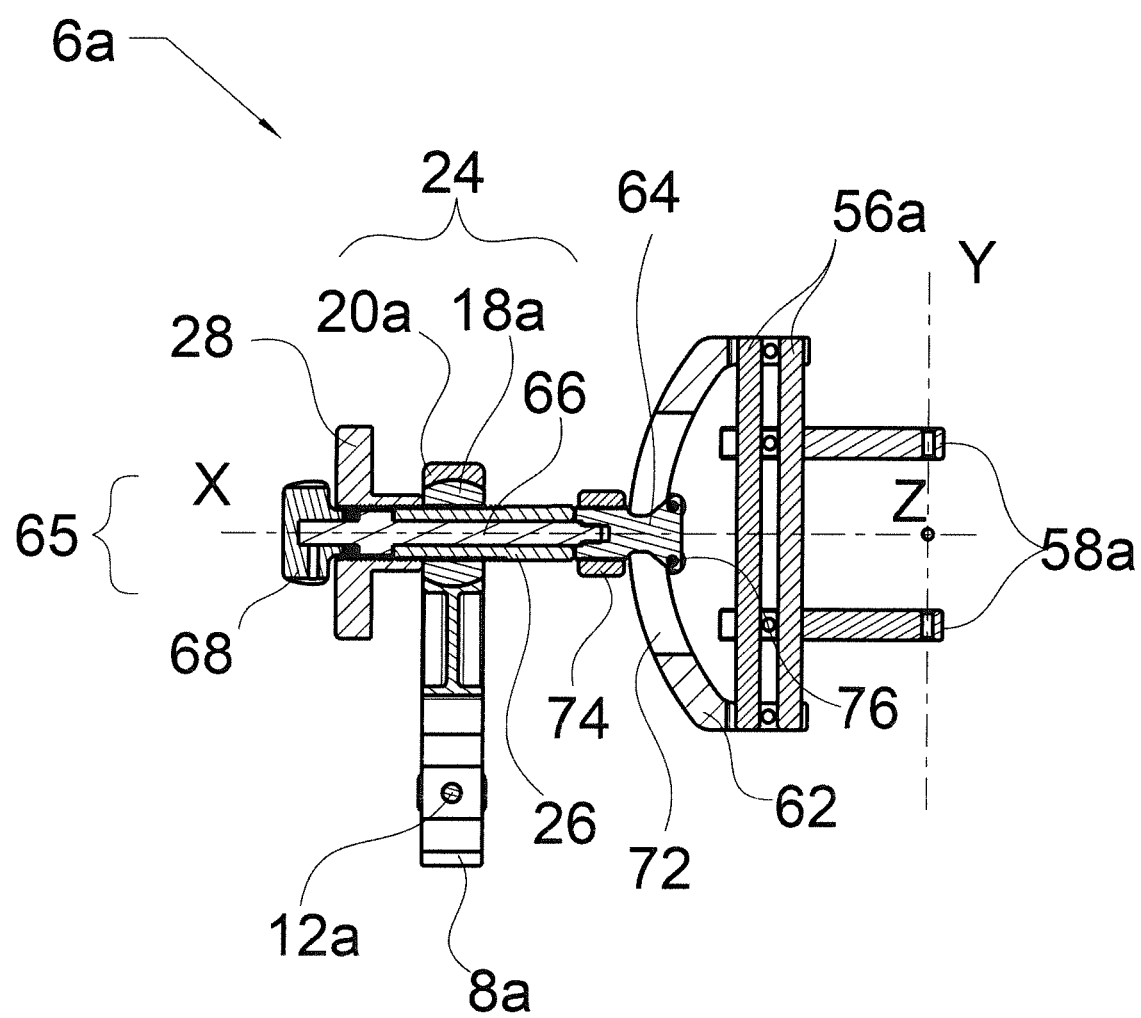
FIG. 7 shows a cross section of a carriage assembly of the embodiment of FIGS. 4-6D in a cross-section along the longitudinal axis of the medical positioning device.

FIG. 6D shows the fully assembled medical positioning device 2. The carriages 8a, 8b are attached to the balls 18a, 18b via the respective sockets 20a, 20b. The carriages 8a, 8b are also attached to the base frame 10.

A correct orientation and attachment of the carriages 8a, 8b to the support members 14a, 14b is enabled by the flexibility of the spherical joints 16a, 16b. Once the support members 14a, 14b are connected to one another via the spherical joints 16a, 16b, the carriages 8a, 8b and the base frame 10, the spherical joints 16a, 16b are fixed, for example via joint screws 54.

The user may now start with the actual correction procedure of repositioning the bone parts. The user may reopen one or both of the spherical joints 16 in order to reposition/re-orient one or both of the pins 4. Once the one or more pins 4 are correctly oriented, the respective spherical joints 16 are fixed again. Furthermore, the user may perform a distraction, i.e. increasing the distance between the pins 4. This may be done by accordingly actuating the extension screw 28. Actuation of the extension screw 28 results in a longitudinal movement of the first support member 14a and thus the first pin 4a relative to the base frame 10 and the second pin 4b. The relative movement of the pins 4 is translated into a longitudinal movement of the pinned bone parts relative to one another.

The user may additionally or alternatively adjust the orientation of the first pin 4a via a rotational movement about the longitudinal axis X and/or the transversal axis Z. If a rotation about the longitudinal axis X is desired, the user may open the longitudinal fixation element 68, perform the desired rotation of the support member 14a/pin 4a about the X-axis and close the longitudinal fixation element 68 again in order to provide for a fixation of the pin 4a in the new position. If a rotation about the transversal axis Z is desired, the user may open the transversal fixation element 74, perform the desired rotation of the support member 14a/pin 4a about the Z-axis and close the transversal fixation element 74 again in order to provide for a fixation of the pin 4a in the new position. In this way, the user is able to perform a rotation of the pin about a center of rotation that is located in the bone that needs repositioning. Additionally, the rotation about the longitudinal axis X is independent from the rotation about the transversal axis Z. These properties may further facilitate the repositioning procedure.

Figure 8:
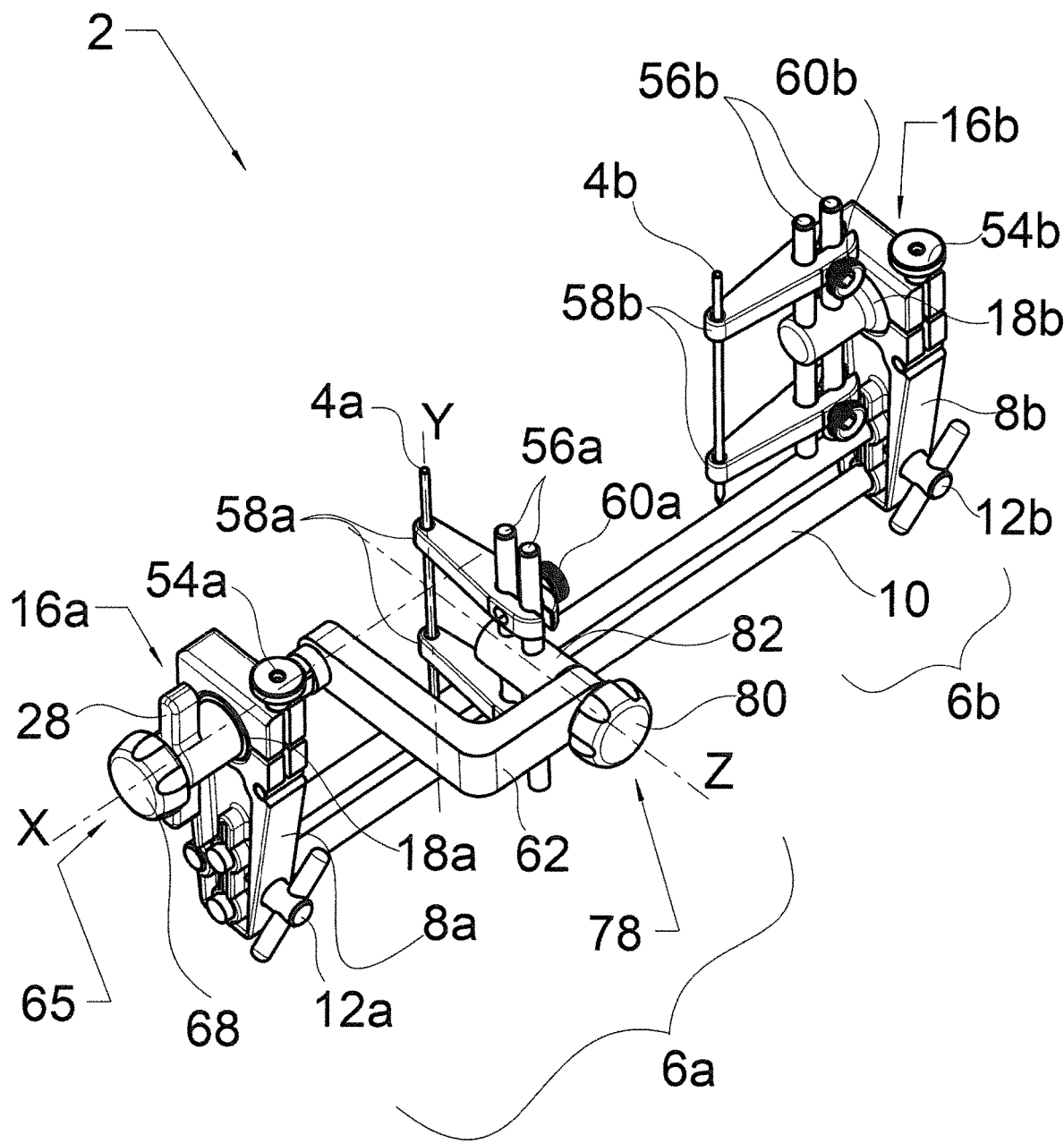
FIG. 8 shows a perspective view of yet another embodiment of the medical positioning device.

FIG. 8 shows a perspective view of another embodiment of the present invention. As the embodiment of FIGS. 4-6D, the embodiment of FIG. 8 provides for independent rotation of one of the pins 4 (here pin 4a) about the longitudinal axis X and the transverse axis Z but based on an alternative mechanism. In FIG. 8, the two independent rotations may be achieved via a cardan joint-like connection. The first carriage assembly 6a comprises an L-shaped support frame 62, which is configured for being mounted to a rotation assembly 65. However, other shapes of the support frame 62 are contemplated. The rotation assembly 65 comprises a longitudinal fixation element 68 and extends through the extension screw 28 and the threaded rod 26. This part of the rotation assembly 65 may be similar to the embodiment in FIGS. 4-6D. Again, the support frame 62 may be rotated about the longitudinal axis X, when the fixation element 68 is in the open state. If the fixation element 68 is in the closed state, rotation of the support frame 62 about the longitudinal axis X is inhibited. Preferably, this is achieved by an equivalent system of two sets of teeth as already described above. In the case of FIG. 8, the sets of teeth are provided on the interface of the rotation assembly with the support frame 62. The effect of opening and closing the fixation element 68 is as already described above: in the open state of the fixation element 68, the two sets of teeth are not engaged and the support frame 62 is free to rotate about the longitudinal axis X, i.e. relative to the rotation assembly 65, and in the closed state, such a rotation is inhibited due to the engagement of the two sets of teeth. Alternatively, a thread may be used without the sets of teeth.

The rotation of the pin 4a about the transversal axis Z may be implemented with a second rotation assembly 78, which is attached to the support frame 62 and extends along the transverse axis Z. The working principle may be analogous to the first rotation assembly 65. The second rotation assembly may, e.g., comprise a second fixation element 80, preferably a screw, and a counterpart 82. The counterpart 82 may be configured for mounting the support rods 56a, which are in turn configured for mounting the support arms 58a. The support arms 58a are configured for holding the pin 4a. The screw 80 may traverse the support frame 62 and engage the counterpart 82 in such a way that the support frame 62 is located between a head of the screw 80 and the counterpart 82. If the second fixation element 80 is in an open state, the counterpart 82, and thus the support rods 56a, the support arms 58a and the pin 4a, may be rotated about the transverse axis Z. If the second fixation element 80 is in a closed state, such rotation is inhibited. Inhibition of the rotation may be achieved with two sets of teeth at the interface of the counterpart 82 and the support frame 62, one set of teeth on the counterpart 82 and one set of teeth on the support frame 62. If the second fixation element 80 is in the closed sate, the screw 80 pulls the counterpart 82 against the support frame 62 such that the sets of teeth are engaged with each other and inhibit a rotation. If the second fixation element 80 is in the open sate, the sets of teeth are not engaged with each other and a rotation is possible.

FIG. 8 shows a second carriage assembly 6b in the right part of the figure. This carriage assembly may be configured as described above, preferably as the second carriage assembly 6b of FIGS. 4-6D.

The invention claimed is:

1. A medical positioning device, comprising:
a first carriage assembly configured for mounting a first pin, wherein the orientation of the first pin is adjustable by a first spherical joint;
a second carriage assembly configured for mounting a second pin, wherein the orientation of the second pin is adjustable by a second spherical joint;
wherein at least one of the first and the second carriage assemblies is configured to rotate the respective first or second pin about at least a first axis crossing the respective first or second pin and about a second axis crossing the respective first or second pin, the second axis extending transversely to the first axis; and
wherein the at least one of the first and the second carriage assemblies is configured to rotate the respective first or second pin about the first axis independent from rotation about the second axis.

2. The medical positioning device of claim 1, wherein the first axis comprises a longitudinal axis of the medical positioning device extending through the respective first spherical joint or the second spherical joint and the second axis comprises a transverse axis of the medical positioning device that is perpendicular to the longitudinal axis.

3. The medical positioning device of claim 1, wherein at least one of the first and the second carriage assemblies comprises a support frame having a guidance, the at least one of the first and the second carriage assemblies further comprising a sliding carriage configured to engage the guidance, wherein movement of the support frame along the sliding carriage provides for rotation of the respective first or second pin about at least one of the first axis and the second axis.

4. A medical positioning device, comprising:
a first carriage assembly configured for mounting a first pin, wherein the orientation of the first pin is adjustable by a first spherical joint;
a second carriage assembly configured for mounting a second pin, wherein the orientation of the second pin is adjustable by a second spherical joint;
wherein at least one of the first and the second carriage assemblies is configured to rotate the respective first or second pin about at least a first axis crossing the respective first or second pin and about a second axis crossing the respective first or second pin, the second axis extending transversely to the first axis; and
wherein the first axis comprises a longitudinal axis of the medical positioning device extending through the respective first spherical joint or the second spherical joint and the second axis comprises a transverse axis of the medical positioning device that is perpendicular to the longitudinal axis.

5. The medical positioning device of claim 4, further comprising a rotation rod configured to rotate about its longitudinal axis such that one of the first pin and the second pin rotates about the longitudinal axis of the medical positioning device, or wherein at least one of the first and second carriage assemblies comprises a rotation assembly, the rotation assembly configured to rotate the respective first or second pin about the longitudinal axis and the transverse axis, respectively.

6. The medical positioning device of claim 4, wherein at least one of the first and the second carriage assemblies comprises a support frame having a guidance, the at least one of the first and the second carriage assemblies further comprising a sliding carriage configured to engage the guidance, wherein movement of the support frame along the sliding carriage provides for rotation of the respective first or second pin about at least one of the first axis and the second axis.

* * * * *